US008805480B2

(12) United States Patent
Hancock et al.

(10) Patent No.: US 8,805,480 B2
(45) Date of Patent: Aug. 12, 2014

(54) TISSUE DETECTION AND ABLATION APPARATUS AND APPARATUS AND METHOD FOR ACTUATING A TUNER

(75) Inventors: Christopher Paul Hancock, Bristol (GB); John Bishop, Bristol (GB)

(73) Assignee: Medical Device Innovations Limited, Halton, Cheshire (GB)

( * ) Notice: Subject to any disclaimer, the term of this patent is extended or adjusted under 35 U.S.C. 154(b) by 1168 days.

(21) Appl. No.: 11/569,622

(22) PCT Filed: May 26, 2005

(86) PCT No.: PCT/GB2005/002085
§ 371 (c)(1),
(2), (4) Date: Nov. 27, 2006

(87) PCT Pub. No.: WO2005/115235
PCT Pub. Date: Dec. 8, 2005

(65) Prior Publication Data
US 2008/0234574 A1    Sep. 25, 2008

(30) Foreign Application Priority Data

May 26, 2004  (GB) .................................. 0411807.1
Sep. 1, 2004  (GB) .................................. 0419417.1

(51) Int. Cl.
*A61B 5/05* (2006.01)
(52) U.S. Cl.
USPC ................ 600/430; 606/33; 606/34; 606/42; 607/101; 607/107; 324/638; 324/642
(58) Field of Classification Search
USPC ......... 600/430; 606/33, 34, 42; 607/101, 107; 324/638, 642
See application file for complete search history.

(56) References Cited

U.S. PATENT DOCUMENTS

| 4,114,623 A | 9/1978 | Meinke et al. |
| 4,209,018 A | 6/1980 | Meinke et al. |
| 4,397,313 A | 8/1983 | Vaguine |
| 4,488,559 A | 12/1984 | Iskander |
| 4,502,028 A | 2/1985 | Leake |
| 4,638,813 A | 1/1987 | Turner |
| 4,658,836 A | 4/1987 | Turner |

(Continued)

FOREIGN PATENT DOCUMENTS

| DE | 3637549 | 5/1988 |
| EP | 0462302 | 12/1991 |
| EP | 0804900 | 11/1997 |
| EP | 0256524 | 2/1998 |
| EP | 1013228 | 6/2000 |
| EP | 1080694 | 3/2001 |
| EP | 1118310 | 7/2001 |
| EP | 1123135 | 8/2001 |
| EP | 1186274 | 3/2002 |
| EP | 1504791 | 2/2005 |
| FR | 2617723 | 1/1989 |

(Continued)

OTHER PUBLICATIONS

Aimoto et al., "Nonoinvasive method for measuring the electrical properties of deep tissues using an open-ended coaxial probe", Institution of Physics and Engineering in Medicine and Biology, Elsevier pp. 1350-1533, 1996.*

(Continued)

*Primary Examiner* — Unsu Jung
*Assistant Examiner* — Joseph M Santos Rodriguez

(57) ABSTRACT

The present invention relates to an apparatus for classifying and/or ablating tissue. By directing microwave radiation through a probe (5) into tissue (6) and detecting the amplitude and phase of radiation reflected back through the probe and a reference signal, the tissue type can be classified. An impedance tuner which is actuated by magnetostrictive material (800) is also disclosed.

16 Claims, 18 Drawing Sheets

(56) References Cited

U.S. PATENT DOCUMENTS

| | | | |
|---|---|---|---|
| 4,825,880 A | 5/1989 | Stauffer et al. |
| 5,057,106 A | 10/1991 | Kasevich et al. |
| 5,108,391 A | 4/1992 | Flachenecker et al. |
| 5,227,730 A | 7/1993 | King et al. |
| 5,249,585 A | 10/1993 | Turner et al. |
| 5,280,429 A | 1/1994 | Withers |
| 5,344,435 A | 9/1994 | Turner et al. |
| 5,364,392 A | 11/1994 | Warner et al. |
| 5,370,678 A | 12/1994 | Edwards et al. |
| 5,405,346 A | 4/1995 | Grundy et al. |
| 5,496,271 A | 3/1996 | Burton et al. |
| 5,507,791 A | 4/1996 | Sit'ko |
| 5,509,916 A | 4/1996 | Taylor |
| 5,518,861 A | 5/1996 | Coveleskie et al. |
| 5,557,283 A | 9/1996 | Sheen et al. |
| 5,693,082 A | 12/1997 | Warner et al. |
| 5,713,946 A | 2/1998 | Ben-Haim |
| 5,720,718 A | 2/1998 | Rosen et al. |
| 5,749,869 A | 5/1998 | Lindenmeier et al. |
| 5,807,257 A | 9/1998 | Bridges |
| 5,810,803 A | 9/1998 | Moss et al. |
| 5,829,437 A | 11/1998 | Bridges |
| 5,868,739 A | 2/1999 | Lindenmeier et al. |
| 5,906,609 A | 5/1999 | Assa et al. |
| 5,944,749 A | 8/1999 | Fenn |
| 5,957,969 A | 9/1999 | Warner et al. |
| 5,991,605 A * | 11/1999 | Rapeli ............................ 455/76 |
| 6,002,968 A | 12/1999 | Edwards |
| 6,016,811 A | 1/2000 | Knopp et al. |
| 6,026,331 A | 2/2000 | Feldberg et al. |
| 6,047,215 A | 4/2000 | McClure et al. |
| 6,148,236 A | 11/2000 | Dann |
| 6,230,060 B1 | 5/2001 | Mawhinney |
| 6,245,062 B1 | 6/2001 | Berube et al. |
| 6,251,128 B1 | 6/2001 | Knopp et al. |
| 6,287,302 B1 | 9/2001 | Berube |
| 6,306,132 B1 | 10/2001 | Moorman et al. |
| 6,311,090 B1 | 10/2001 | Knowlton |
| 6,312,427 B1 | 11/2001 | Berube et al. |
| 6,325,796 B1 | 12/2001 | Berube et al. |
| 6,334,074 B1 | 12/2001 | Spertell |
| 6,345,194 B1 | 2/2002 | Nelson et al. |
| 6,347,251 B1 | 2/2002 | Deng |
| 6,350,276 B1 | 2/2002 | Knowlton |
| 6,383,182 B1 | 5/2002 | Berube et al. |
| 6,413,255 B1 | 7/2002 | Stern |
| 6,421,550 B1 | 7/2002 | Palmer |
| 6,448,788 B1 | 9/2002 | Meaney et al. |
| 6,456,064 B1 * | 9/2002 | Dore et al. ............... 324/207.13 |
| 6,463,336 B1 | 10/2002 | Mawhinney |
| 6,470,217 B1 | 10/2002 | Fenn et al. |
| 6,471,696 B1 | 10/2002 | Berube et al. |
| 6,477,426 B1 | 11/2002 | Fenn et al. |
| 6,527,768 B2 | 3/2003 | Berube et al. |
| 6,582,426 B2 | 6/2003 | Moorman et al. |
| 6,635,055 B1 | 10/2003 | Cronin |
| 6,652,520 B2 | 11/2003 | Moorman et al. |
| 6,663,622 B1 | 12/2003 | Foley et al. |
| 6,684,097 B1 | 1/2004 | Parel et al. |
| 6,690,181 B1 | 2/2004 | Dowdeswell et al. |
| 6,699,237 B2 | 3/2004 | Weber et al. |
| 6,813,515 B2 | 11/2004 | Hashimshony |
| 6,962,587 B2 | 11/2005 | Johnson et al. |
| 7,344,533 B2 | 3/2008 | Pearson et al. |
| 2001/0016762 A1 | 8/2001 | Carr |
| 2001/0020178 A1 | 9/2001 | Arndt et al. |
| 2001/0020180 A1 | 9/2001 | Arndt et al. |
| 2001/0029368 A1 | 10/2001 | Berube |
| 2001/0034519 A1 | 10/2001 | Goble et al. |
| 2001/0039416 A1 | 11/2001 | Moorman et al. |
| 2001/0044643 A1 | 11/2001 | Litovitz |
| 2002/0022836 A1 | 2/2002 | Goble et al. |
| 2002/0043326 A1 | 4/2002 | Bright |
| 2002/0058932 A1 | 5/2002 | Moorman et al. |
| 2002/0065529 A1 | 5/2002 | Laurent et al. |
| 2002/0072645 A1 | 6/2002 | Chronenky et al. |
| 2002/0087151 A1 | 7/2002 | Mody et al. |
| 2002/0091427 A1 | 7/2002 | Rappaport et al. |
| 2002/0120261 A1 | 8/2002 | Morris et al. |
| 2002/0128642 A1 | 9/2002 | Berube et al. |
| 2002/0128648 A1 | 9/2002 | Weber et al. |
| 2002/0133151 A1 | 9/2002 | Hung et al. |
| 2002/0134779 A1 | 9/2002 | Furtlehner et al. |
| 2002/0156511 A1 | 10/2002 | Habib |
| 2002/0165529 A1 | 11/2002 | Danek |
| 2002/0193783 A1 | 12/2002 | Gauthier et al. |
| 2002/0193786 A1 | 12/2002 | Berube et al. |
| 2002/0193849 A1 | 12/2002 | Fenn et al. |
| 2003/0004454 A1 | 1/2003 | Fenn et al. |
| 2003/0065317 A1 | 4/2003 | Rudie et al. |
| 2003/0069575 A1 | 4/2003 | Chin et al. |
| 2003/0069619 A1 | 4/2003 | Fenn et al. |
| 2003/0073988 A1 | 4/2003 | Berube et al. |
| 2003/0130711 A1 * | 7/2003 | Pearson et al. ............... 607/101 |
| 2003/0195500 A1 | 10/2003 | Moorman et al. |
| 2004/0087936 A1 | 5/2004 | Stern et al. |
| 2004/0186470 A1 | 9/2004 | Goble et al. |
| 2004/0210214 A1 | 10/2004 | Knowlton |
| 2004/0215235 A1 | 10/2004 | Jackson et al. |
| 2004/0215296 A1 | 10/2004 | Ganz et al. |
| 2004/0243200 A1 | 12/2004 | Turner et al. |
| 2005/0080466 A1 | 4/2005 | Homer |

FOREIGN PATENT DOCUMENTS

| | | |
|---|---|---|
| GB | 2126901 | 4/1984 |
| GB | 2387544 | 10/2003 |
| GB | 2406521 | 4/2005 |
| JP | 06-076962 | 3/1994 |
| JP | 06-119265 | 4/1994 |
| JP | 7-204209 | 8/1995 |
| JP | 9-117456 | 5/1997 |
| JP | 9-117457 | 5/1997 |
| JP | 10-137258 | 5/1998 |
| JP | 2001-029356 | 2/2001 |
| WO | WO 92/04934 | 4/1902 |
| WO | WO 80/01461 | 7/1980 |
| WO | WO 81/02841 | 10/1981 |
| WO | WO 81/03616 | 12/1981 |
| WO | WO 81/03617 | 12/1981 |
| WO | WO 92/04934 | 4/1992 |
| WO | WO 97/07621 | 5/1992 |
| WO | WO 93/00132 | 1/1993 |
| WO | WO 93/08876 | 5/1993 |
| WO | WO 94/26188 | 11/1994 |
| WO | WO 95/18575 | 7/1995 |
| WO | WO 96/40369 | 12/1996 |
| WO | WO 97/43971 | 11/1997 |
| WO | WO 99/05978 | 2/1999 |
| WO | WO 00/47280 | 8/2000 |
| WO | WO 00/53113 | 9/2000 |
| WO | WO 01/58373 | 8/2001 |
| WO | WO 01/62169 | 8/2001 |
| WO | WO 01/72084 | 9/2001 |
| WO | WO 03/024309 | 3/2003 |
| WO | WO 03/096919 | 11/2003 |
| WO | WO 03092609 | 11/2003 |
| WO | WO 03/101324 | 12/2003 |
| WO | WO 2004/047659 | 6/2004 |
| WO | WO 2004/064606 | 8/2004 |
| WO | WO 2004/066947 | 8/2004 |
| WO | WO 2004/071317 | 8/2004 |
| WO | WO 2004/084748 | 10/2004 |
| WO | WO 2005/030071 | 4/2005 |

OTHER PUBLICATIONS

Hoshi et al., Application of Microwaves and Millimeter Waves for the Characterization of Teeth for Dental Diagnosis and Treatment, *IEEE Transactions on Microwave Theory and Techniques*, vol. 46, No. 6, Jun. 1998.

* cited by examiner

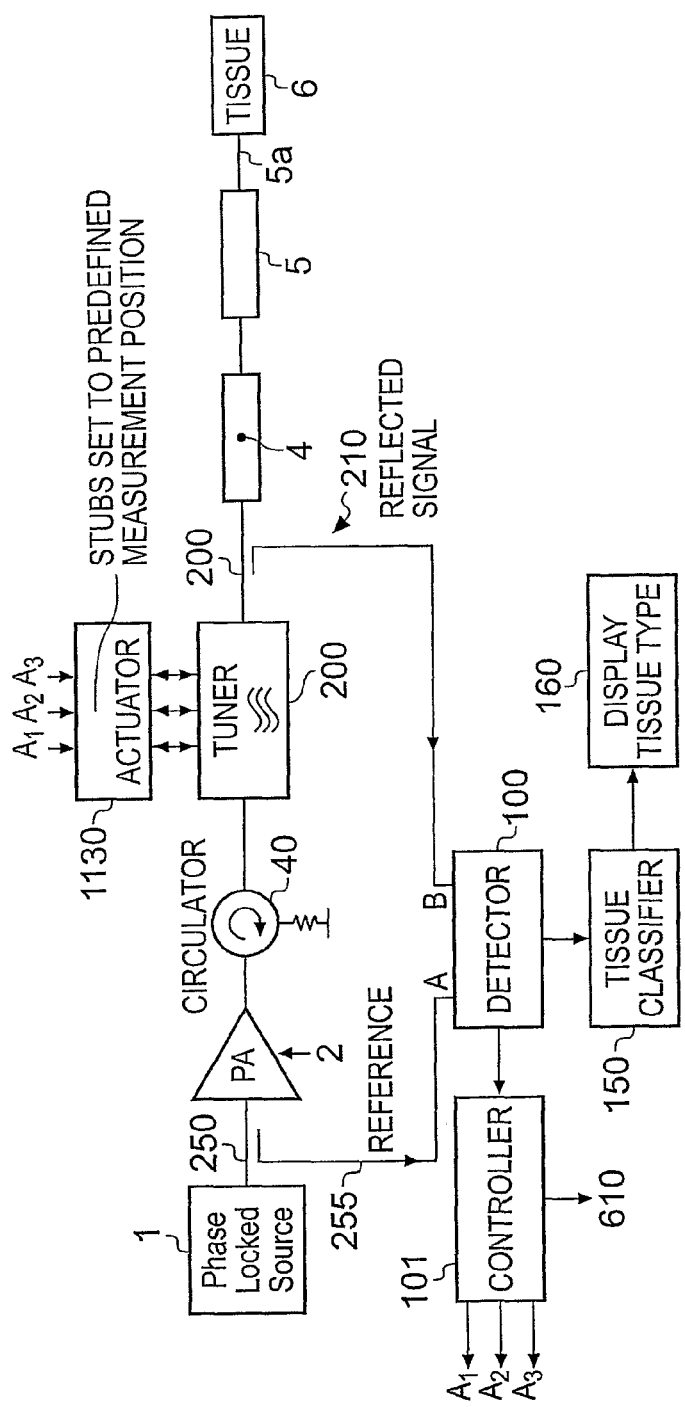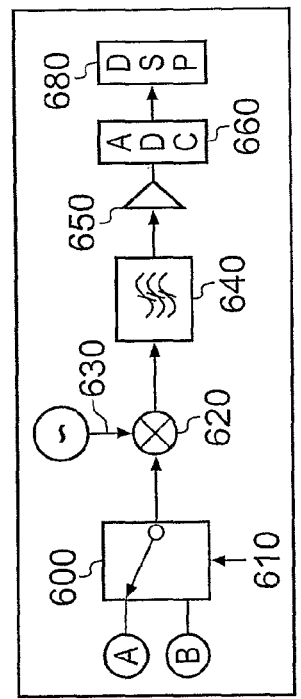
Fig. 5
Fig. 5a

Table A

| Measurement Set A | | Impedance | | Polar | | Cartesian | |
|---|---|---|---|---|---|---|---|
| Group | Material | r (ohms) | jx (ohms) | Mag. (mV) | Phase (deg.) | I (mV) | Q (mV) |
| a | Air | 49.0 | 0.2 | 9.9 | 166.0 | -9.6 | 2.4 |
|   | Air Ref. | 50.6 | -0.9 | 10.4 | -55.7 | 5.9 | -8.6 |
| b | Lard | 66.3 | 1.6 | 140.5 | 4.8 | 140.0 | 11.8 |
|   | Oil | 68.5 | -0.9 | 156.4 | -2.4 | 156.3 | -6.5 |
| c | Jelly | 58.1 | -26.0 | 244.9 | -59.1 | 125.8 | -210.1 |
| d | Egg White | 52.1 | -31.2 | 293.4 | -69.2 | 104.2 | -274.3 |
|   | Pork | 51.5 | -32.7 | 306.7 | -69.6 | 106.9 | -287.5 |
|   | Liver | 52.1 | -32.5 | 303.7 | -68.7 | 110.3 | -283.0 |
|   | Water | 51.6 | -33.2 | 310.6 | -69.2 | 110.3 | -290.4 |

Table B

| Measurement Set B | | Impedance | | Polar | | Cartesian | |
|---|---|---|---|---|---|---|---|
| Group | Material | r (ohms) | jx (ohms) | Mag. (mV) | Phase (deg.) | I (mV) | Q (mV) |
| a | Air | 31.3 | 0.1 | 230.5 | 179.7 | -230.5 | 1.2 |
|   | Air Ref. | 31.3 | 0.2 | 230.7 | 179.2 | -230.7 | 3.2 |
| b | Lard | 36.3 | 9.1 | 189.5 | 140.2 | -145.6 | 121.3 |
|   | Oil | 36.2 | 8.7 | 187.9 | 141.9 | -147.9 | 115.9 |
| c | Jelly | 51.0 | -1.7 | 19.4 | -60.0 | 9.7 | -16.8 |
| d | Egg White | 54.6 | -8.0 | 87.7 | -55.7 | 49.4 | -72.4 |
|   | Pork | 54.4 | -7.8 | 85.2 | -56.4 | 47.1 | -71.0 |
|   | Liver | 54.4 | -6.9 | 78.2 | -53.5 | 46.5 | -62.9 |
|   | Water | 55.2 | -7.7 | 87.8 | -51.7 | 54.4 | -68.9 |

Fig. 7

Table C

| Measurement Set C | | Impedance | | Polar | | Cartesian | |
|---|---|---|---|---|---|---|---|
| Group | Material | r (ohms) | jx (ohms) | Mag. (mV) | Phase (deg.) | I (mV) | Q (mV) |
| d | Egg White | 40.2 | 29.2 | 324.4 | 90.6 | -3.4 | 324.4 |
|  | Pork | 39.5 | 28.3 | 321.7 | 92.9 | -16.3 | 321.3 |
|  | Liver | 39.3 | 26.9 | 310.5 | 94.8 | -26.0 | 309.4 |
|  | Water | 36.3 | 26.6 | 331.6 | 100.2 | -58.7 | 326.4 |

Table D

| Measurement Set D | | Impedance | | Polar | | Cartesian | |
|---|---|---|---|---|---|---|---|
| Group | Material | r (ohms) | jx (ohms) | Mag. (mV) | Phase (deg.) | I (mV) | Q (mV) |
| d | Egg White | 42.5 | 4.4 | 93.8 | 146.5 | -78.2 | 51.8 |
|  | Pork | 41.1 | 4.3 | 108.6 | 151.5 | -95.4 | 51.8 |
|  | Liver | 40.3 | 3.5 | 114.7 | 158.0 | -106.3 | 43.0 |
|  | Water | 38.3 | 4.4 | 141.3 | 156.4 | -129.5 | 56.6 |

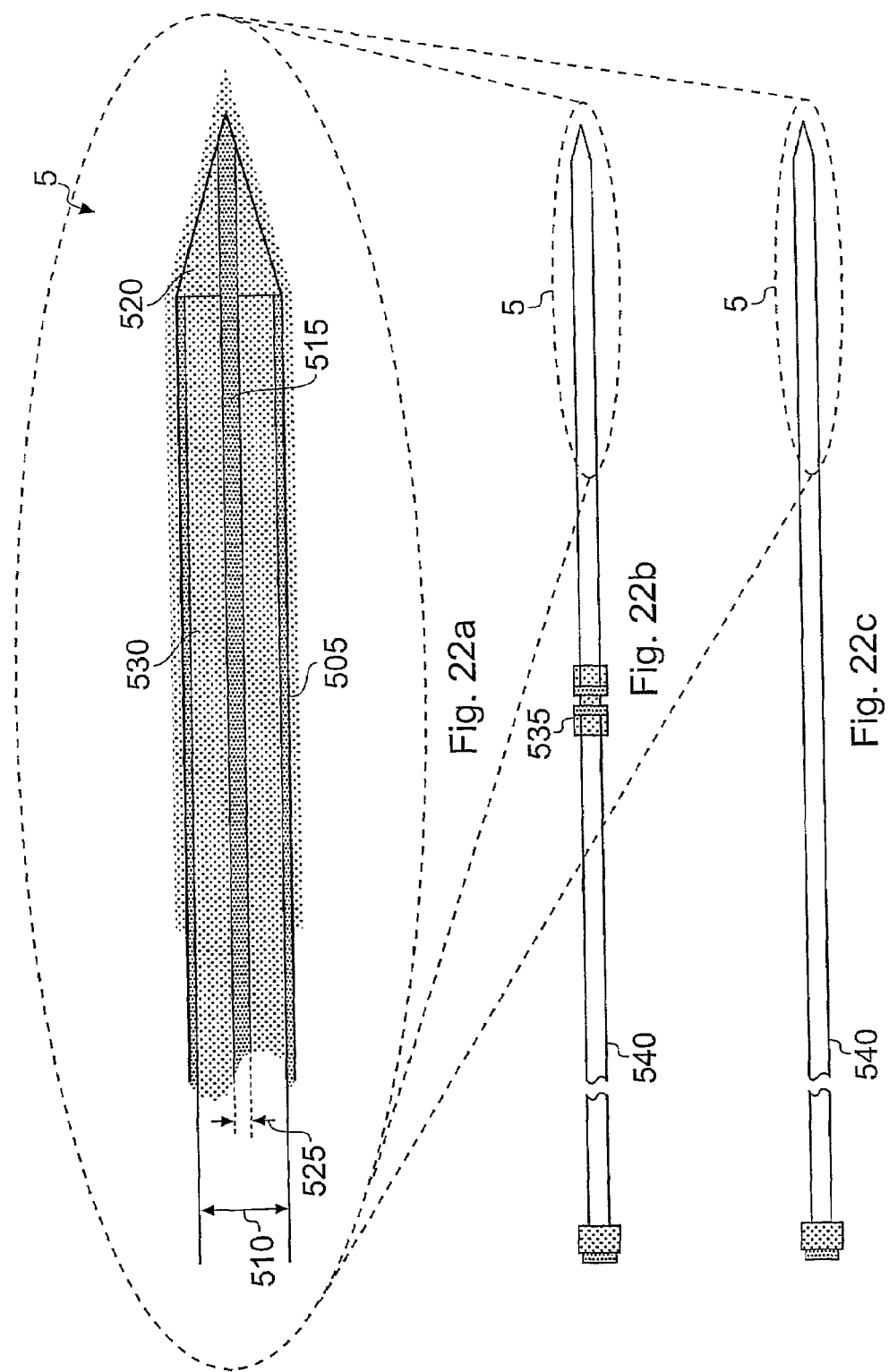

TISSUE DETECTION AND ABLATION APPARATUS AND APPARATUS AND METHOD FOR ACTUATING A TUNER

TECHNICAL FIELD

The present invention relates to an apparatus which uses microwave radiation to detect and classify tissue into one or more types or states and/or ablate the tissue. It also relates to an actuation device and method for actuating a tuner for use in such an apparatus. In this specification microwave means the frequency range from 5 GHz to 60 GHz inclusive. Preferably 14-15 GHz is used, but the present invention is not limited to this narrower range.

BACKGROUND TO THE INVENTION

International application PCT/GB2003/005166 filed on 27 Nov. 2003, disclosed a tissue ablation apparatus having a tuning circuit for matching the impedance of the apparatus with that of the tissue being ablated to perform efficient energy transfer into the tissue and minimise heating of the apparatus. One version of the apparatus is shown in FIG. 1.

As shown in FIG. 1 the apparatus has a stable source of microwave radiation 1 connected to an ablation probe 5, for directing the microwave radiation into tissue, via a triple stub tuner 50 having an adjustable impedance. The apparatus achieved the impedance matching by varying the impedance of the triple stub tuner 50 on the basis of the detected phase and magnitude of a signal reflected back through the ablation probe 5 and directed to a detection arrangement 220, 240, 270 by a directional coupler 200. It was necessary to detect both the magnitude and phase of the reflected signal, so that an accurate impedance adjustment could be made. This was achieved by mixing the reflected signal with a signal from a local oscillator 270 in a mixer 220, so that the phase and magnitude could be provided at the detector 240 by heterodyne detection. The processor 101 then controlled the actuator 1130 to make the appropriate adjustment to the impedance of the tuner 50, so that impedance matching was achieved. The phase and magnitude of a forward directed signal (from source towards the probe) could also be measured by a detection system 230, 260, 280 and taken into account in determining the impedance adjustment.

PCT/GB2003/005166 taught that it was desirable to phase lock the source of microwave radiation 1 (in FIG. 1), for example by using the feed back loop configuration shown in FIG. 3, where the source is a VCO whose frequency is reduced by a frequency divider and compared in a phase comparator with a stable (e.g. crystal) local oscillator signal; the phase comparator outputs a signal via amplifier and filter arrangement 1010 to control the VCO whereby its frequency is kept stable. As an alternative it would be possible to combine a broad band source 1030 with a narrow band filter 1140 as shown in FIG. 4. The purpose of the configurations shown in FIG. 3 and FIG. 4 is to provide a stable source of microwave radiation, so that variations in the source frequency do not disrupt the signal detection.

In summary PCT/GB2003/005166 taught detecting a reflected signal from the probe and using information in that signal to adjust the impedance of a tuning element in the circuit. By adjusting the impedance to match that of the tissue being ablated, energy efficiency of the apparatus could be achieved.

SUMMARY OF THE INVENTION

However, the inventors have realised that the reflected radiation could be used not only to effect impedance matching of the probe and the tissue, but also to detect characteristics of the tissue at the end of the probe. For example, by analysing the reflected radiation it would be possible to determine the type of tissue. It should also be possible to distinguish between different types or states of the tissue, e.g. to distinguish between cancerous tissue and healthy tissue. This should allow an operator of the apparatus to know when the probe reaches cancerous tissue that needs to be ablated, avoid accidentally ablating healthy tissue and may also inform the operator when cancerous tissue has been fully ablated so that the ablation operation can be stopped. The invention could also be applied outside the context of an ablation system, e.g. as a standalone tissue measurement or classifying system. The inventors have realised that absolute magnitude measurements alone are not sufficient for this purpose; both the real and imaginary components of a complex impedance need to be taken into account.

Accordingly a first aspect of the present invention provides a tissue classifying apparatus comprising a source of microwave radiation having a given frequency, a probe for directing the microwave radiation into tissue;

a detector for detecting the magnitude and phase of a reflected signal comprising microwave radiation reflected back through said probe and the magnitude and phase of a reference signal; and a tissue classifier for classifying the tissue into a tissue type or tissue state on the basis of the magnitude and phase of the signals detected by said detector.

The apparatus according to the first aspect of the present invention is suitable for making in vivo measurements of tissue in a human or animal body. The probe is designed for insertion into tissue. By the above configuration the apparatus is able to determine what type of tissue (e.g. bone, fat, muscle, tumour) is at the end of the distal end of the probe. The distal end of the probe may have a centre conductor, which is conductively or capacitively loaded.

The reference signal may be derived from the source of microwave radiation (e.g. a portion of the forward directed signal diverted to the detector by a directional coupler). Alternatively the reference signal may be derived from a separate source (e.g. an independent local oscillator). A switch can be used to multiplex the reflected and reference signals to the detector. Furthermore, there may be several possible reference signals (e.g. taken from different locations on the signal path between the source and the probe) and a switch multiplexing between them. The detector may comprise a phase comparator, a vector network analyser, a processor for analysing the input signals and/or a heterodyne detection configuration using local oscillators and mixers.

Preferably the tissue classification is carried out on the basis of a complex impedance (having both real and imaginary components) calculated from the magnitude and phase of the reflected and reference signals and a first set of data relating to known or theoretical values for the complex impedance of one or more tissues types. These values, or data from which the theoretical complex impedance of tissue types can be calculated, can be found in texts such as Physical Properties of Tissue: A Comprehensive Reference Book by Francis A Duck, Academic Press London, 1990, ISBN 0-12-222800-6; chapter 6 of this book provides specific information about the electrical properties of tissues, including conductivity and relative permittivity.

These texts give theoretical values and known values for single homonogenous tissue samples measured under controlled in vitro conditions, e.g. in isolated holding cassettes etc. It is expected that the actual values measured in vivo will be different, due to blood flow, multiple tissue layers and other considerations, but still related to these known values.

Preferably the tissue classification takes into account a predetermined relationship between values in said first data set and values in a second data set relating to the complex impedances of known tissue types measured by the apparatus (or previously measured by another apparatus according to the present invention). In this way a few measurements made with the apparatus can be extrapolated to give expected values for other tissue types.

Alternatively the tissue classifier could classify the tissue by comparing the measured complex impedance with values in a table assigning predetermined values or ranges of values to different tissue types (or states).

Preferably the apparatus is calibrated by measuring the complex impedance at the distal end of the probe (from the phase and magnitude of the reflected and reference signals) for a known impedance—e.g. air or a suitable known material. Future measurements can then be referenced to this calibration value. The distal end of the probe may be enclosed by the calibration material (where it is not air). Calibration is necessary because different probe types and cable set ups will change the complex impedance measured, e.g. each additional length causes the phase to rotate and probe cable dielectric and conductor losses cause the magnitude to decrease. The calibration may be carried out with reference to a single known complex impedance, but preferably two (or more) different materials having different complex impedances are used (e.g. air and a hair or a piece of fixed permittivity foam). In the case where air and a piece of fixed impedance material are used, the tip of the probe is enclosed by the fixed impedance material.

Preferably there is an impedance tuner between the source and the probe. This may be a stub tuner, most preferably a triple stub tuner. The presence of a tuner enables the circuit impedance of the apparatus to be adjusted to give maximum sensitivity for carrying out tissue measurements. When there is an impedance tuner, calibration may be carried out by adjusting the complex impedance of an impedance tuner until the measured impedance of the/these known material(s) at calibration is equal to the expected (known) impedance. Other methods of calibration will be apparent to a person skilled in the art. For example, where a stub tuner is used, the stubs can be adjusted until a single known position is obtained (e.g. 50 ohms+j0, but not limited to that value), which is then used to compare what is seen at the end of the probe.

If the apparatus has an adjustable impedance tuner, then the impedance of the tuner is preferably kept constant while the apparatus is classifying tissue (e.g. if it is a stub tuner the stubs are kept stationary). This helps to make the measurements accurate and repeatable. The complex impedance of the tuner used during tissue classification should be the same as that used during calibration. The impedance tuner may be controlled by any suitable actuation means, e.g. a stepper motor, linear motor, piezo electric actuator, moving coil or magnetostrictive actuator. A magnetostrictive actuator is especially advantageous and is discussed in more detail later.

Where a stub tuner is used, the stub positions could initially be set to enable a maximum phase-magnitude change when the probe is inserted into various tissue layers or where there is a change in tissue state during ablation.

The apparatus preferably comprises a flexible cable for channeling the microwave radiation to the probe. This cable may be a waveguide or a coaxial cable. The cable will be coupled to the source of microwave radiation and the detector, usually there are one or more intermediate components between the cable and the source of microwave radiation (e.g. amplifiers, circulators, an impedance tuner etc). The cable may be connected to the output of the impedance adjuster. Preferably the probe is integral with the flexible cable (in which case the probe is a rigid or semi-rigid portion and the cable is a flexible portion).

Preferably the cable has a high phase stability under flexure. This is advantageous because phase measurement is necessary to classify the tissue, but the cable will flex (e.g. twist and turn) as the probe is maneuvered by the operator. If phase is shifted due to flexing of the cable, then information is lost.

Preferably the phase stability of the cable with flexing is ±5° or less at the frequency of microwave radiation which is conveyed to the probe (i.e. the frequency of the source of microwave radiation). This means that the phase shift experienced by microwave radiation travelling through the cable, due to flexing of the cable, is ±5° of phase or less. More preferably ±3° or less, even more preferably ±2° or less.

A standard method for measuring the phase stability of a cable under flexure is to flex the cable by +90° and then by −90°, repeat 100,000 times and measure the phase shift in a signal passed through the cable during the flexing. The flexing of ±90° is carried out around a mandrel having a diameter of 4 inches (101.6 mm). The maximum phase shift measured during this test is the phase shift specified as the cable's phase stability under flexure.

Phase stability varies with the frequency of the signal. The above preferred phase stabilities are specified for the frequency with which the cable will be used in practice when the apparatus is in use. It should be noted however, that phase stability decreases with increasing frequency. That is, if a cable has the required phase stability at 40 GHz then it will certainly have the required phase stability at 14 GHz, as there will be less variation of phase with flexing at the lower frequency.

It is also preferable that the cable has amplitude stability under flexure. Preferably the amplitude stability under flexure is 2.8 dB or less (meaning that no more than 2.8 dB in signal amplitude is lost due to cable flexure). More preferably no more than 1.5 dB, even more preferably no more than 1.2 dB, most preferably no more than 1 dB. Amplitude stability with flexure can be measured in the same way as for phase stability above (except that change in amplitude is measured instead of change in phase).

If there are two different sources of microwave radiation with different frequencies (one for ablation, one for tissue classification—as will be discussed below), then the cable should have the required phase and amplitude stability at the frequency which is used for tissue classification. Preferably cable will have phase and amplitude stability for both frequencies.

The source of microwave radiation is preferably arranged to output a single stable frequency. By single stable frequency it is meant that its output frequency does not vary by more than ±5 MHz over the operating temperature range of the apparatus (usually 22° C. to 60° C.), at constant load. More preferably the frequency does not vary by more than ±1 MHz, still more preferably no more than ±500 kHz, ±50 kHz, ±10 kHz or even as little as ±1 kHz over the operating temperature range.

The advantage of having a single frequency source is that many microwave components have frequency dependent properties. For example, many microwave components including directional couplers, wave guide sections, tuner cavities, E-field launchers, cable assemblies, adaptors, probe assemblies and attenuation pads exhibit frequency dependent insertion loss and/or impedance. The latter can cause frequency dependent changes in the impedance match/mismatch and the voltage standing wave ratio. These factors change the microwave measurement information, which is extracted from the apparatus. For example, the reflected signal (and also the reference signal, if it is derived from the source of microwave radiation) will generally be diverted to the detector by couplers and will therefore be a function of the directivity (ability to differentiate between forward and reflected signals) and the coupling factor (portion of the main signal diverted) of the couplers, both of which are frequency dependent. Accordingly, variation in source frequency causes a change in system characteristics, which manifests itself as noise or reduced system sensitivity, leading to reduced measurement sensitivity and a limitation in the ability to differentiate between certain tissue types. For example, a change in the source frequency during the period of time between the reference signal measurement and the reflected signal measurement will lead to power and phase changes between the reference and reflected signals (in addition to any changes caused by interaction the tissue) and such unwanted changes are difficult to recognise and compensate for. These problems are avoided if the source outputs a single stable frequency as defined above.

Preferably the source of microwave radiation is phase locked to a single frequency. This source may be arranged so that the single frequency to which the source is locked can be varied by the user (e.g. the user may be able to choose a frequency in the range 13.75 to 14.75 GHz). Preferably the source of microwave radiation is phase locked to a crystal oscillator. Most preferably the crystal oscillator is itself phase locked to another crystal oscillator. This double phase locking arrangement helps to further guarantee stability of the output signal.

Alternatively the source may be a broadband source coupled to a narrow band filter.

The detector may comprise an analogue detector, but preferably comprises a processor, phase comparator, vector network analyser or other electronic device arranged for measuring the phase and magnitude of input signals. Current electronic devices tend to require relatively low frequencies and therefore the frequency of the reflected signal, and usually the reference signal as well, needs to be reduced before input into the detector. This may be achieved by using a frequency divider, but that adds noise to the system.

Therefore another approach is to mix the reflected signal by combining it with a mixing down signal of different frequency in a mixer. The output from the mixer is then at a lower frequency which can be accepted by the detector. The mixing down signal's frequency can be chosen such that it mixes with the reflected and/or reference signal(s) to produce a frequency suitable for input to the detector. It will usually be desirable to provide one or more filters for filtering out unwanted frequencies and a digital to analogue converter between the output of said mixer and the (electronic) detector.

The mixing down signal may be provided by a local oscillator (e.g. a local oscillator having a different frequency to the source of microwave radiation). However, there the phase and frequency of the local oscillator and the source of microwave radiation may drift apart and this will reduce the accuracy of the measurements made. Accordingly it is preferred that the mixing down signal is derived from the source of microwave radiation.

Therefore the apparatus preferably comprises a mixer having first and second inputs and an output, the first input being coupled to a pathway for conveying said reflected signal to the mixer, the second input being coupled to a pathway for conveying a mixing down signal to the mixer and the output being coupled to the detector.

Preferably the mixing down signal is derived from the source of microwave radiation.

Preferably the pathway for delivering the mixing down signal to said mixer comprises a phase locked loop for controlling the frequency of the mixing down signal on the basis of the frequency of the source of microwave radiation. This helps to reduce or prevent drift of the mixing down signal, which might otherwise cause inaccuracies in the measurement.

As explained above the detector classifies the tissue on the basis of a reference signal and the reflected signal. However, the detector may use more than one reference signal. That is, it may be advantageous for the apparatus to have first and second reference signal sources, which input respective signals to the detector (or to two separate detectors).

In one embodiment the first reference signal is derived from the source and an independent local oscillator generates the second reference signal. Alternatively the second reference signal may be derived from the source of microwave radiation and mixed with a local oscillator to provide a different frequency. The first and second reference signals should have different frequencies. The tissue classifier can then classify the tissue on the basis of the magnitude and phases of the reflected signal and the first and second reference signals. The advantage of having a second reference signal is that more information can be extracted from the phase and magnitude measurements and this enables the tissue to be characterised (and its complex impedance measured) more accurately. The second reference signal is also helpful if there is a lot of noise or systematic errors in the system.

Preferably the probe is inserted into the centre of the tissue being classified, so that its measurement part is not crossing a junction between different tissue types. This makes it possible to disregard tissue interface effects.

The detection apparatus may be an integral part of an apparatus for ablating tissue with microwave radiation. It is convenient to combine the two functions in a single system. Therefore the apparatus is preferably capable of both ablating tissue and classifying tissue into one of several tissue types.

A second aspect of the present invention provides an apparatus for ablating tissue comprising an apparatus according to the first aspect of the present invention wherein the probe is adapted for delivering microwave radiation into tissue so as to ablate said tissue. The apparatus preferably further comprises an impedance adjuster (e.g. a tuner) having an adjustable complex impedance, said adjuster being located between said source and said probe.

In this way the impedance adjuster (tuner) can have its complex impedance adjusted on the basis of the signals detected by said detector (a controller may be provided for this purpose). Any suitable actuator may be used as discussed under the first aspect. Thus, impedance matching between the probe and the tissue can be achieved, so as to ensure efficient transmission of the microwave radiation into the tissue and minimise heating of the apparatus. Furthermore, in use, the apparatus can detect the type of tissue that the probe is in contact with and the operator can thus decide whether or not to ablate.

Preferably the apparatus is capable of both classifying and ablating tissue. This may be done simultaneously, e.g. by ablating the tissue with microwave radiation and classifying it on the basis of the reflected signal (and a separate reference signal). Preferably however, the apparatus has separate ablation and tissue classification modes. For example the operator could switch the apparatus between an ablation mode for ablating the tissue and a tissue characterising mode for classifying the tissue. In the tissue characterisation mode, the impedance of the tuner is preferably kept constant, so that the reflected signal can be compared to a constant reference as discussed above under the first aspect. In the ablation mode, the impedance of the tuner is preferably varied by the controller in order to match the impedance of the tissue being ablated. In general the power of the microwave radiation directed through the probe in the classifying mode is much less than the power in the ablation mode, so that the tissue can be measured, but not damaged.

As there can be a big difference in amplitude between the signal strength in the ablation and classification modes, this may cause difficulties in signal detection when the same apparatus is used to detect and analyse both reflected ablation and reflected tissue classification signals. This is especially the case where a mixer is used to mix down the reflected frequency before input to the detector, because mixers usually only operate over a limited dynamic range. Therefore the apparatus preferably comprises (i) a variable amplifier for amplifying the reflected microwave radiation before it reaches the detector when the apparatus is in the tissue classification mode and/or (ii) a variable attenuator for attenuating the reflected microwave radiation before it reaches the detector when the apparatus is in the tissue ablation mode. In this way the signal strength can be adjusted before it reaches the detector or mixer. A separate detector may be used to check the original signal strength before amplification or attenuation so that this information can be stored or passed on to the controller or an operator.

The apparatus may be arranged to direct a first frequency of microwave radiation to the probe when in the ablation mode and a second frequency of microwave radiation, different to the first frequency, to the probe when in the tissue classification mode. For example, the apparatus may have a first source of microwave radiation to be used for ablating tissue and having a first frequency, and a second source of microwave radiation to be used for classifying tissue and having a second frequency. Said second frequency is different from said first frequency and is used for tissue measurement and classification purposes. The advantage of this is that certain tissue types may give a particularly strong response at certain frequencies, which makes those frequencies good for tissue classification, but a different frequency may be better for ablation.

The second source of microwave radiation is coupled to the probe and a return path for conveying reflected radiation of the second frequency couples the probe to the detector. A second reference signal, preferably derived from the second source of microwave radiation, is provided as a reference for the reflected microwave radiation of the second frequency. Tissue classification can then be carried out as described above.

One or more filters may be provided to prevent or minimise the first frequency reaching inputs of the detector reserved for the second frequency and vice versa. This enables both sources of microwave radiation to be switched on at once, e.g. so that tissue ablation and classification can be carried out simultaneously.

The term probe means any device, which is capable of delivering microwave radiation into tissue and receiving microwave radiation reflected by the tissue. The probe may, for example, be coaxial or it may be a waveguide. Preferably, the waveguide is loaded with a low loss dielectric and/or magnetic material; this to enables the size of the waveguide cavity to be reduced. The probe should be suitable for insertion into tissue and suitable for use in invasive procedures. Preferably the probe is designed to be capable of penetrating tissue. For example, the probe preferably has a rigid casing enabling it to be inserted into tissue without the aid of an endoscope or trocar. However, it would be possible for the probe to be semi-rigid or flexible and be inserted into the body through a trocar, endoscope, cannula or other tube. The probe is preferably tapered, pointed or cone shaped at its distal end. This helps the probe to penetrate tissue and also focuses the microwave radiation. However, it is not necessary for the probe to be cone shaped, pointed or tapered, especially where it is designed for insertion into tissue through an endoscope or other tube. In any case, the procedure is preferably invasive, that is the probe is first inserted into the tissue, either directly or through a tube, and microwave energy is then delivered for ablation or tissue classification purposes.

Preferably the probe has an outer conductor, an inner conductor and a dielectric between the two, and a cone is attached to the distal end of the structure.

Preferably the cone comprises a low loss dielectric (low loss at GHz frequencies). Preferably the inner conductor is exposed at the distal end of the probe. Preferably the inner conductor extends through the cone and most preferably it is exposed at the distal end of the cone. It has been found that this provides optimal measurement sensitivity.

Preferably the probe is integrated with a flexible cable (which may e.g. be connected to the tuner output). This enables the cable and probe assembly to be sterilised together, which is convenient for the operator.

The apparatus of the second aspect of the invention may have any of the features of the first aspect mentioned above.

PCT/GB2003/005166 described impedance matching by adjustment of the impedance of a tuner. However, the mechanism for adjusting the impedance was not discussed in detail. As tissue relaxation times are very short, of the order of ms, the actuation of the tuner needs to be equally quick if it is to keep up with changes in the tissue's complex impedance. At its most general, a third aspect of the present invention proposes the use of magnetostrictive material in the actuator. Magnetostrictive materials change their dimensions when exposed to a magnetic field. They respond very quickly to changes in a magnetic field and accordingly a quick adjustment of impedance can be achieved.

Accordingly, a third aspect of the present invention may provide a tuner for use in a microwave circuit having one or more tuner elements (e.g. tuner rods) of adjustable length or position, so that by adjustment of said elements the impedance of the tuner can be varied; and at least one actuator comprising a length of magnetostrictive material coupled to one of said tuning elements so that changes in length of said magnetostrictive material move or change the effective length of said tuning element; and one or more sources of electric current connected to one or more coil windings surrounding at least a portion of said magnetostrictive material. The sources of electric current can then be used to generate the magnetic field via the coil windings and to change the length of the magnetostrictive material.

The, or each, tuning element may be integral with a respective magnetostrictive actuator. However, as most magnetostrictive materials will cause signal loss in the tuner, it is preferable that the actuator(s) and the tuning elements are separate components. Low loss materials, e.g. silver and copper, are especially suitable for the tuning elements. If the tuning element and actuator are one integral component then it is preferable that a tuning end of the component is coated in a low loss material so as to avoid losses in the tuner. In this case the coating thickness is preferably such that the electromagnetic field is at or near zero at the coating element interface.

Usually each actuator will have several coil windings or sets of coil windings surrounding its magnetostrictive material. Preferably there are a plurality of current sources and each is connected to a respective separate coil winding or set of coil windings. In this way the number of windings coupled to each current source can be kept low and the response time is kept short; another advantage is that the levels of induced emf are minimised. Each current source may take the form of a respective amplifier connected to a FPGA/DSP or other control circuit for controlling the current directed to each current winding. Fast amplifiers with high output voltage and high slew rates are preferred.

Preferably the magnetostrictive material comprises terfenol, most preferably terfenol-D. Other magnetostrictive materials could be used, for example Nickel, Iron & Permalloy. Terfenol-D is preferred because it has a very high bulk saturation strain ($2000 \times 10^{-6}$) and so can provide very quick actuation.

In one embodiment the length of magnetostrictive material is a rod, one end of which is attached to a tuning element.

Preferably the length of magnetostrictive material is housed in a non-magnetic housing, for example a hollow cylinder of a non-magnetic metal or plastic material. The coil windings can be provided on the outside of the housing.

Preferably the housing has an interference (i.e. tight) fit with the magnetostrictive material. That is it grips the actuator. This enables the actuator (e.g. rod of magnetostrictive material) to move along a bore of the housing. Each time current is pulsed through one or more coils a magnetic field is generated and the actuator expands. After the pulse has passed, the material relaxes and the actuator contracts.

The effect is that the actuator can be moved along the bore. When the pulses have a first polarity the actuator expands towards a first end of the bore so as to push the tuning element further into the tuner. After the pulse passes the magnetostrictive material relaxes its 'front' end is gripped by the housing and the back end (opposite the direction of expansion) contracts and is pulled up to the new position. In this way the actuator advances along the bore. If the polarity is changed then the expansion and relaxation is in the opposite direction and the tuning element can be retracted.

Accordingly the actuator is preferably a moveable actuator in the form of a rod magnetostrictive material which is moveable along the bore of a housing, with which it has an interference fit, by pulsing of a magnetic field. This arrangement allows a large degree of movement compared to the situation if one end of the actuator was fixed at a fixed position in the housing.

By activating each current source (and coil or coil set) independently it is possible to cause each succeeding cross-section of the magnetostrictive rod to elongate, then contract when the field is removed, causing the rod to crawl down the bore of the housing.

Preferably, the tuning elements are tuning rods of a stub tuner, most preferably a triple stub tuner. Each tuning rod or element is coupled to a respective magnetostrictive actuator.

The tuner and actuation arrangement of the third aspect of the present invention may be used with either a tissue ablation apparatus or a tissue classification apparatus or an apparatus, which is capable of both tissue classification and ablation. For example it may be used with an apparatus according to the first or second aspects of the present invention.

The tuner of the third aspect of the present invention could also be used in a tissue ablation apparatus comprising a source of microwave radiation, a probe for directing the microwave radiation into the tissue to be ablated, a detector for detecting the magnitude and phase of microwave radiation reflected back through the probe and an impedance tuner between the probe and the source. A controller could then control the actuator(s) to adjust the impedance of the tuner on the basis of the detected phase and magnitude of the reflected microwave radiation. In this way the impedance of the apparatus can be matched with the tissue being ablated even if the complex impedance of the tissue changes rapidly. The detector may be a phase comparator or vector network analyser. The detector may be a heterodyne detection arrangement comprising a mixer and a local oscillator of a frequency different to that of the source of microwave radiation.

A fourth aspect of the present invention provides a tissue ablation or measurement apparatus comprising a source of microwave radiation, a probe for directing the microwave radiation into the tissue to be ablated, a detector for detecting the magnitude and phase of microwave radiation reflected back through the probe and an impedance tuner between the probe and the source, wherein the impedance tuner comprises one or more rods which are actuated by one or more actuators comprising magnetostrictive material.

Preferably the impedance tuner is a tuner according to the third aspect of the present invention.

A fifth aspect of the present invention is a method of classifying tissue comprising the steps of a) inserting a probe into tissue to be classified, b) directing microwave radiation through said probe into the tissue, c) classifying the tissue type or tissue state based on the amplitude and phase of microwave radiation reflected by said tissue back through said probe and the amplitude and phase of a reference signal. The method may use an apparatus according to the first aspect of the present invention.

The probe may be configured to penetrate tissue and inserted directly into the tissue. Alternatively it may be inserted via a tube such as a trocar or an endoscope.

The distal end of the probe should be positioned in the tissue which is to be classified.

A sixth aspect of the present invention may provide a method comprising the steps of, firstly classifying the tissue by carrying out the steps of the fifth aspect of the present invention and then ablating the tissue by directing microwave radiation down the same probe or another probe inserted into said tissue.

In this way the apparatus can be used to locate a tissue of a particular type which is to be ablated (e.g. to locate a tumour or cancerous tissue), before starting the ablation.

Example of applications to which this method can be applied include the following: neurosurgery and the treatment of brain tumours, hepatic surgery such as the treatment of hepatocellular carcinoma, treatment of desmoid tumours, oesophageal carcinoma, lung carcinoma and breast carcinoma. In each case the cancerous tissue can be located and subsequently ablated by the apparatus.

It would also be possible to locate the cancerous tissue by using an apparatus according to the fifth aspect of the present invention and then use other conventional surgical methods to remove or destroy the tissue.

A further application is to relieve pain by identification and ablation of nerve pathways. For example, it would be possible to relieve chronic and intractable pain in patients with advanced carcinoma that has progressed to invasion of nerve plexii. Selective ablation of the plexii would destroy the nerve pathways. Such treatment would not prolong the patient's life, but could potentially improve the patient's quality of life by alleviation of the pain.

Preferably the tissue classification is carried out with microwave radiation of a first power and the ablation is carried out with microwave radiation of a second power greater than said first power.

The method may comprise a further step of classifying the tissue after ablation has been carried out for a certain period of time, in order to check whether or not all of the tissue which it is desired to ablate (e.g. cancerous tissue) has been ablated. This tissue classification may be carried out periodically, e.g. after a set period of ablation, e.g. by stopping the ablation and switching to classification mode. Alternatively it may be carried out continuously at the same time as ablation where different frequencies are used for tissue ablation and classification.

The operator may continue to ablate after it is detected that all of the desired (e.g. cancerous) tissue is ablated, in order to establish a safe margin around the original tumour to make sure that no cancerous tissue is left.

The sixth aspect of the present invention may be carried out using an apparatus according to the second aspect of the present invention.

A seventh aspect of the present invention is a method of actuating an impedance tuner using magnetostrictive material as described above under the third aspect of the present invention. This may be combined with the fifth and sixth aspects discussed above.

Another aspect of the present invention, relating to mixing down of reflected and/or reference signals in ablation or tissue classification apparatus, will now be described. As previously mentioned, PCT/GB2003/005166 disclosed that it would be possible to use a magnitude/phase comparator 65, as shown in FIG. 2, instead of the heterodyne detection system shown in FIG. 1. In FIG. 2 directional couplers 250, 200 direct portions of the forward and reflected signal to the detector arrangement, which includes amplitude sensors 61, 63 for measuring the magnitude of the signals as well as the phase comparator 65 for measuring the phases. Because currently available phase comparators can only handle relatively low frequencies, it would be necessary to reduce the frequency of the reflected signal from coupler 200 by using an electronic frequency divider 64.

However, electronic frequency dividers introduce significant amounts of phase noise when large division ratios are used (and other random noise such as thermal and junction noise is introduced), and so information is lost. Therefore the inventors have devised a system that uses a mixing arrangement instead of an electronic frequency divider, to reduce the frequency. In this system, the reflected microwave radiation is mixed with a second microwave signal of a different frequency, from a local oscillator, such that the mixer outputs a signal of a lower frequency to be used in the detector. A difficulty is that the phase and frequency of the local oscillator and the source of microwave radiation will drift and this will reduce the accuracy of the measurements made.

Therefore one aspect of the present invention proposes that the second signal (which may be called a 'mixing down' signal) is derived from and preferably phase locked to the source of microwave radiation. In this way, the measurement is kept accurate, as any difference in phase should be due to interaction with the tissue, not due to temporal variations between two different oscillators (which might happen if the mixing down signal was provided by an independent local oscillator). Furthermore, mixing down in this manner provides more useful information, as information would be lost if a frequency divider was used.

Accordingly, an eighth aspect of the present invention proposes a tissue ablation or measurement apparatus comprising:

a source of microwave radiation;
a probe for delivering said microwave radiation to tissue to be ablated and/or measured;
a first pathway for conveying microwave radiation from said source to said probe;
a first mixer having first and second inputs and an output;
a second pathway for delivering a signal derived from said source to said first input of said first mixer; and
a third pathway for diverting a portion of microwave radiation from said first pathway, said diverted radiation being either forward directed radiation travelling along said first pathway from said source to said probe or reflected microwave radiation reflected back through said probe, and delivering said diverted radiation or a signal derived from the diverted radiation to said second input of said first mixer;
the output of the mixer being arranged to send a signal to a processor which is configured to calculate the amplitude and phase of said forward or reflected radiation diverted from said first pathway;
wherein said second pathway comprises a phase locked loop for controlling the frequency of the signal sent to the first input of the first mixer on the basis of the frequency of the source of microwave radiation.

This aspect of the present invention may be applied to a tissue ablation apparatus, a tissue classification apparatus, or an apparatus which is capable of both classifying and ablating tissue.

Generally, the signal input to the first mixer's first input should be different in frequency to the signal input to the first mixer's second input as the mixer outputs the difference and the sum of the two input frequencies, the latter of which is preferably filtered out with a low pass filter. Usually said second pathway is configured such that it delivers a signal, having a different frequency than the frequency of the source of microwave radiation, to said first input of said first mixer. The signal input to the second input of the first mixer is usually the same frequency as the source of microwave radiation. The difference between the two signal frequencies should be acceptable for input to the processor either directly or via an ADC. In essence the second path delivers a mixing down signal to the first mixer, where it is mixed with a reflected or reference signal diverted from the first path.

Preferably the phase locked loop comprises a forward path and a feedback path. Preferably the forward path comprises a second mixer having a first input coupled to said source of microwave radiation and an output for outputting a signal from said second mixer along the forward path towards said first input of said first mixer; the feedback path being arranged to divert a portion of the signal sent to the first input of said first mixer to a second input of said second mixer.

In other words it is preferable that the second path is coupled to the source of microwave radiation and has a second mixer between the source of microwave radiation and the first mixer; there being a fourth path coupling the first input of the first mixer with the second input of the second mixer. This fourth path is in effect the feedback path mentioned above (as part of the second path's phase locking loop). This is a convenient way of implementing the phase locked loop. It provides a stable frequency for the first input of the first mixer, which is referenced to said first frequency.

Preferably the forward path comprises a phase detector and a voltage controlled oscillator. These may conveniently be posited between the first and second mixers. The phase detector may be connected to or comprise a local oscillator, and configured for comparing the phase of the signal output from the second mixer with the phase of the local oscillator. It can then deliver a control signal to a voltage-controlled oscillator (VCO) based upon this comparison, the voltage-controlled oscillator being configured to output a signal to the first input of said first mixer.

In this way by appropriate control of the VCO, the frequency sent to the first input of the first mixer can be controlled and prevented from drifting relative to the source of microwave radiation. The local oscillator may be a high accuracy temperature compensated crystal oscillator (e.g. 50 MHz or less), such crystal oscillators provide a much more stable signal than most microwave frequency oscillators and so any variance in the frequency of the source of microwave radiation can be tracked and reflected in the signal sent to the first input of the first mixer, i.e. the intermediate frequency (If) at the output of said first mixer can be kept constant.

Preferably the voltage-controlled oscillator is configured to output a frequency in the microwave range, most preferably close to the frequency of the source of microwave radiation. Specifically, a frequency that will mix in the first mixer with the signal from the third pathway to produce a signal which will be accepted by an ADC or other signal processing device. Usually this will be in the MHz range (e.g. up to 250 MHz, more usually 50 MHz or less, but not limited to either of these).

Preferably a low pass filter is provided between the second mixer and the phase detector. This filters out any high frequency components generated in the second mixer (e.g. filters out the sum of the two input frequencies allowing the difference to pass through) if the sum frequency is outside the frequency band of the first mixer than the low pass filter may not be required.

Preferably a loop filter is provided between the phase detector and the voltage-controlled oscillator. This ensures that the signal from the phase detector is filtered and offset, where necessary, to provide a control signal that can be accepted by the voltage-controlled oscillator.

Preferably there is an analogue to digital converter (ADC) between the output of the first mixer and the processor. This enables an analogue signal from the first mixer to be processed by the processor. The ADC may be integrated into a FDGA, DSP or other form of processor.

It is worth noting that the source of microwave radiation itself is preferably kept stable by its own phased locked loop. That is it is controlled on the basis of feedback on the difference between its phase and that of a stable (e.g. temperature compensated crystal) local oscillator. Another possibility is to have a broadband source filtered by a narrow band filter to give a stable output. The same techniques as described above under the first aspect of the invention may be used in order to achieve a stable single frequency source of microwave radiation.

Preferably there is a circulator on the first pathway, positioned between the source of microwave radiation and the second pathway on the one hand and the probe on the other. In an ablation system, there will usually also be a power amplifier on the first path between the source and the probe and this will generally be placed on the source side of the circulator so as to prevent large levels of reflected power from damaging an output stage of the power amplifier.

Preferably the third pathway comprises a plurality of channels each coupled to a different point on the first pathway or to the probe and connected to a switching device which is configured to direct radiation from only one of said channels at a time to the second input of the first mixer.

Thus the switching device allows selection of the point in the circuit from which the reflected or forward directed radiation is taken. Preferably a controller controls the switching device in conjunction with the detector to take successive readings from different channels. In other words a time multiplexing system is used. Alternatively frequency multiplexing or another multiplexing system could be used.

In this way, as there are several channels, more information is available to analyse the tissue's complex impedance. Generally some of the channels will be connected to the first pathway by forward couplers and will carry forward directed radiation, others will be connected by reverse couplers and channel reflected radiation. The forward directed radiation can act as a reference signal for the reflected radiation whereby the tissue can be classified.

Instead of time-multiplexing it would be possible to have a separate feedback loop comprising first and second mixers for each channel, e.g. 10 mixers and 5 feedback loops if there were five channels for diverting radiation from the first pathway. However, there would then be independent noise or error contributions from each mixer. So multiplexing with a switching device is preferred.

Where there is a circulator, those channels which channel reflected radiation will be coupled to the first pathway at points between said circulator and the probe, or directly to the probe itself. Where there is a power amplifier on the first pathway between the source and the probe, it is preferable that the channels for channeling forward directed radiation on the third pathway are coupled to the first pathway between the output of the power amplifier and the probe. This is because phase changes can occur in the power amplifier, and for purposes of tissue characterisation (see below) and ablation matching it can be more useful to compare the amplified forward directed signal sent towards the probe with the reflected signal passed back through the probe.

The apparatus of the eighth aspect of the present invention may be used to impedance match or to make tissue measurements and classify the tissue or both. Preferably the apparatus is capable of classifying the tissue and comprises a channel for conveying a reference signal to said detector and a tissue classifier for classifying the tissue into a tissue type or tissue state on the basis of the magnitude and phase of the reflected radiation and the reference signal as detected by said detector. The reference signal may be from an independent local oscillator or may derived from the source of microwave radiation, it is however separate from said second pathway. Preferably it is a forward directed signal based on radiation travelling from the source to the probe, usually taken from after any power amplifier as discussed above. Such reference signals can also be used for impedance matching.

As the apparatus is suitable for making in vivo measurements of tissue in a human or animal body, the probe is designed for insertion into tissue. By the above configuration the apparatus is able to determine what type of tissue (e.g. bone, fat, muscle, tumour) is at the end of the distal end of the probe. The distal end of the probe may be made very short by inductively or capacitively loading its centre conductor.

Preferably the apparatus is configured to measure the tissue's complex impedance on the basis of the magnitude and phase of the reference signal and magnitude and phase of radiation reflected back through the probe by the tissue.

Both impedance matching, when ablating tissue, and tissue measurement for the purposes of classifying the tissue involve determining the amplitude and phase of the reflected microwave radiation (or a signal based on the reflected microwave radiation).

The eighth aspect of the present invention may applied either to a tissue ablation apparatus or a tissue measurement apparatus. The apparatus preferably has dual-functionality and is able to both ablate and classify tissue. However this is not compulsory and the present invention may be applied to a tissue measurement apparatus, which does not ablate (e.g. without a high power amplifier) or to a tissue ablation apparatus that does not have the computational capacity to classify the tissue.

A system which is capable of both tissue ablation and classifying tissue will generally have at least two modes of operation: a tissue ablation mode and a tissue classification mode. The power of the microwave radiation output from the probe (and delivered to the tissue) in the ablation mode is typically much higher than the power used in the tissue classification mode. In this way damage to any healthy tissue (e.g. discovered when carrying out tissue classification) can be minimised. It also helps to ensure that high doses of non-ionised radiation are only launched into cancerous tissue.

However, if a mixer is used to convert the reflected radiation to a lower frequency signal that can be accepted by a digital processor then a problem arises between these two modes. Typically a mixer will only be able to operate with a limited dynamic range of input powers. A dynamic range of −10 dB to +10 dB is typical for example.

Therefore another aspect of the present invention proposes, at its most general, that a variable attenuator and/or variable amplifier is/are used to increase or decrease the amplitude of signals directed to the mixer.

Accordingly a ninth aspect of the present invention provides a tissue classification and ablation apparatus comprising a source of microwave radiation;

a probe for delivering said microwave radiation to tissue to be ablated and/or measured;

a first pathway for conveying microwave radiation from said source to said probe;

a first mixer having first and second inputs and an output for directing a signal to said processor;

a second pathway for delivering a signal source to said first input of said first mixer; and said signal having a different frequency to the frequency to the microwave radiation delivered through the probe a third pathway for diverting a portion of microwave radiation from said first pathway, said diverted radiation being either forward directed radiation travelling along said first pathway from said source to said probe or reflected microwave radiation reflected back through said probe, and delivering said diverted radiation or a signal derived from the diverted radiation to said second input of said first mixer;

the output of the mixer being arranged to send a signal to a processor which is configured to calculate the amplitude and phase of said forward or reflected radiation diverted from said first pathway; and a variable attenuator and/or a variable amplifier on said third pathway for attenuating or amplifying the reflected microwave radiation before it reaches the second input of said first mixer.

The signal sent to first input of the first mixer should be different to the frequency input to the second input of the first mixer so that the first mixer can output the difference between the two input signals. Usually this will be achieved by configuring the second pathway to deliver a frequency different to the source of microwave radiation, as the radiation from third pathway will usually have the same frequency as said source. It would in principle be possible to have a frequency divider or mixing down arrangement on the third pathway however. In this second aspect of the invention, the signal from the second pathway, which is delivered to the first input of the first mixer, may be derived from the source of microwave radiation or from a separate independent oscillator.

Preferably the variable attenuator has at least a first attenuation level or range and a second attenuation level or range, and the apparatus is configured to utilise the first attenuation level or range in the classification mode and the second (higher) attenuation level or range in the ablation mode.

The same is true for the variable amplifier except that the amplifier is configured to use greater gain in the classification mode where the incoming signal is weaker.

Generally there will be a power amplifier on the first pathway between the source and the probe. This power amplifier may be switched on or off or preferably has variable gain or is connected to a variable gain amplifier, so as to provide at least two different signal powers for the ablation and tissue characterisation modes. Alternatively or additionally a variable attenuator could be provided between the source of microwave radiation and said amplifier. Other ways of providing the apparatus with first and second power levels for the two different modes, will be apparent to a person skilled in the art.

Preferably a circulator is provided between the power amplifier and the probe.

Preferably the variable attenuator has a continuously variable attenuation (i.e. it is not limited to just two discrete levels of attenuation). In one embodiment the variable attenuator is a pin diode.

Preferably there is an amplitude detector for detecting the reflected signal's amplitude, coupled to the third pathway. The amplitude detector may for example be a logarithmic type or simple diode type, the former will give a large dynamic range, other possibilities will be apparent to a person skilled in the art. The amplitude detector is configured to send a signal for controlling the variable attenuator's attenuation or the variable amplifiers gain on the basis of the detected amplitude. Thus if the amplitude detector detects a large signal it can control the variable attenuator to increase the attenuation so that the signal input into the second input of the first mixer is within a predetermined range. If a very low signal is detected then the variable amplifier can be controlled to amplify the signal to a level acceptable for the second input of the first mixer and the attenuator (if present) can be controlled not to attenuate or for minimal attenuation.

The amplitude detector may be connected to a controller, such as an FPGA, which is configured to control the variable attenuator and/or variable amplifier on the basis of the amplitude detector signal.

The apparatus preferably has an impedance tuner on the first pathway between the source and the probe (where a circulator is present, said impedance tuner will be on the probe side of the circulator). The complex impedance of the impedance tuner is adjustable by the controller on the basis of the amplitude and phase of the reflected microwave radiation as detected by the processor and/or the second, amplitude detector. Preferably the tuner is a triple stub tuner.

The apparatus according to the ninth aspect of the present invention may be used or combined with any of the other aspects of the present invention.

BRIEF DESCRIPTION OF THE DRAWINGS

Embodiments of the present invention will now be described, by way of example only, with reference to the accompanying drawings in which:

FIG. 5 shows a tissue classification apparatus according to a first embodiment of the present invention;

FIG. 7 shows tables of results of complex impedance measurements taken with an apparatus according to the present invention;

FIG. 22($a$) is a cross section of a type of probe, which may be used with the present invention;

FIG. 22($b$) is a diagram of the probe of FIG. 22($a$) together when attached to a flexible cable assembly; and FIG. 22($c$) is a diagram of the probe of FIG. 22($a$) when it is formed integrally with a flexible cable assembly.

DETAILED DESCRIPTION OF THE INVENTION

Figure 1:
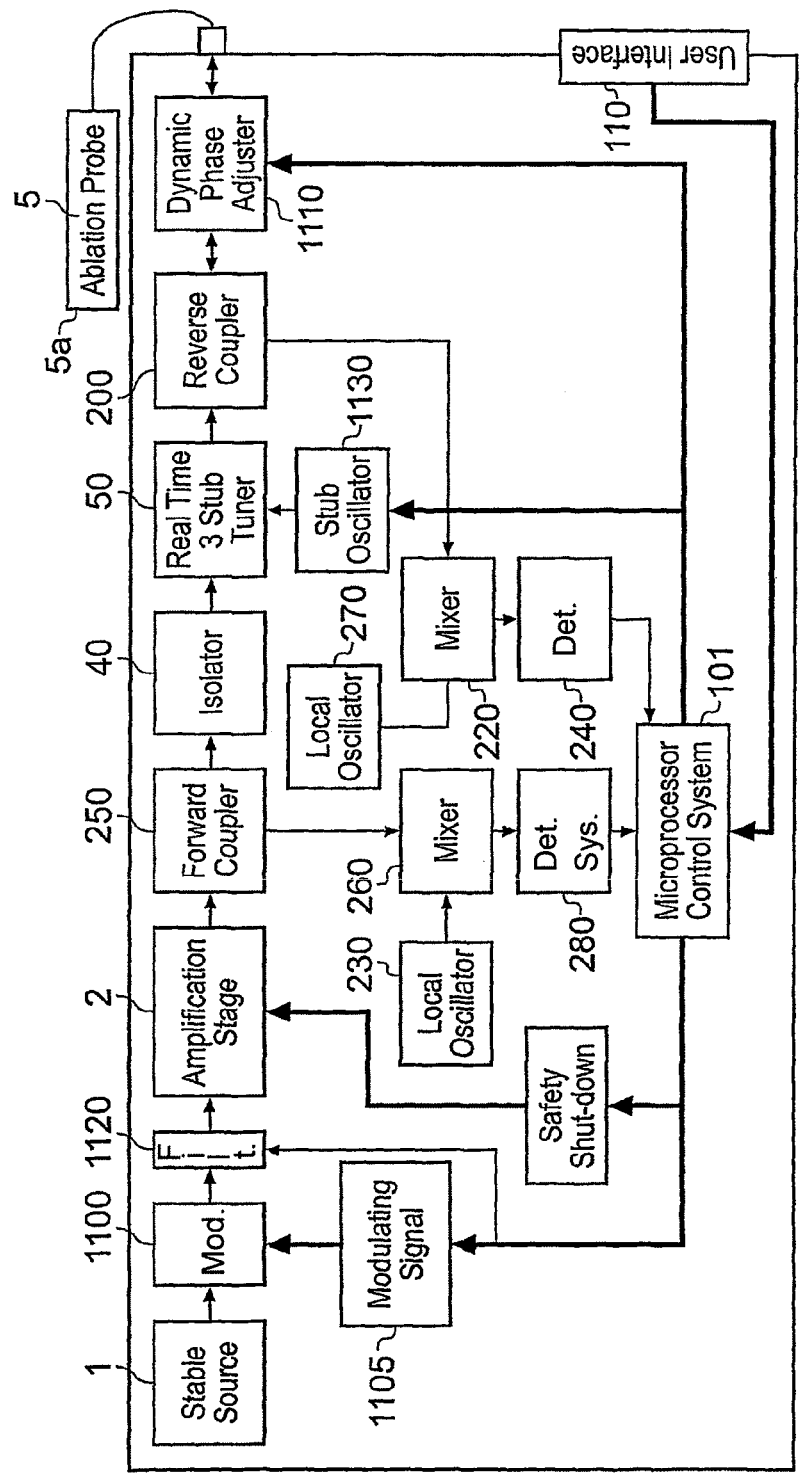
FIG. 1 is an ablation apparatus capable of impedance matching with the tissue at the end of the probe and has already been described.

A tissue classification apparatus, shown schematically in FIG. 5, has a stable phase locked source of microwave radiation 1 connected to a probe 5 configured for directing the microwave radiation into tissue to be classified. The probe 5 is adapted for insertion into the tissue, so that the tissue measured is at or surrounding the distal end 5$a$ of the probe. That is, in use, there is physical contact between the probe and the tissue 6.

The source of microwave radiation 1 may be a voltage controlled oscillator (VCO), a dielectric resonator oscillator (DRO), surface acoustic wave oscillator (SAW), a gunn diode oscillator or any other appropriate oscillator known to a person skilled in the art. The source may comprise a microelectromechanical (MEM) device arranged to act as a frequency control element. MEM devices have the advantage that they are virtually parasitic-free passive devices and so noise and subsequent frequency variation, for example jitter, may be further reduced.

The source of microwave radiation is phased locked so that it outputs a single stable frequency. For example, the arrangement used in FIG. 3 may be used. In the present embodiment, the source of microwave radiation outputs a frequency of between 13.75 GHz and 14.75 GHz, and is phase locked to produce a single frequency of 14.5 GHz. A suitable choice for the source of microwave radiation would, for example, be the Hittite HMC398QS16G VCO, which has a drift of 1.5 GHz/° C. in the operating temperature range. A phase locking arrangement is then used to keep the drift in the output frequency below 5 KHz/degree Celsius in the operating range 20 to 60 degrees Celsius.

Alternatively, the source of microwave radiation may be phased locked to a stable crystal oscillator which is itself phased locked to another stable crystal oscillator (so the configuration has the microwave oscillator and two crystal oscillators). This double phase locking arrangement helps to minimise the drift even further. Minimisation of drift is important because it makes it easier to compensate for noise in the system (which may be frequency dependent) and leads to more accurate measurement sensitivity. One of the crystal oscillators would be a TXCO (temperature compensated crystal oscillator) and the other a VXCO (voltage controlled crystal oscillator). An example of a suitable TXCO is Golledge Electronics Limited's GTXO-580V/G which operates at 13 MHz (but the present invention is not limited to this).

Figure 20:
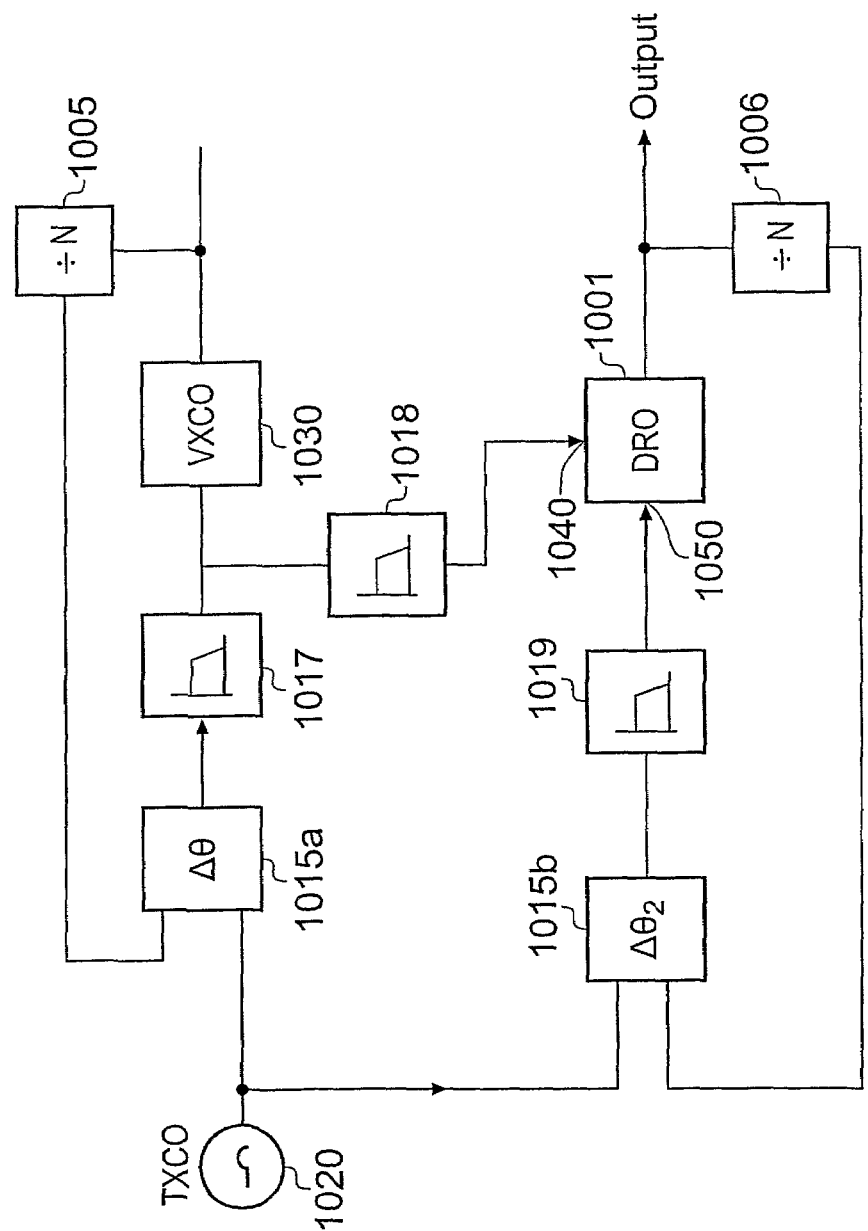
FIG. 20 is an example of a double phase locked arrangement for the source of microwave radiation.

FIG. 20 shows an example of a double phase locked arrangement. It comprises a DRO (Dielectric Resonator Oscillator) 1001 which acts as the source of microwave radiation, a TXCO 1020 which acts as the first crystal oscillator and a VXCO 1030 which acts as the second crystal oscillator.

The first crystal oscillator 1020 outputs a signal (at a set stable frequency, typically in the MHz range) to phase comparator 1015$b$. The phase comparator 1019 outputs, via loop filter 1019, to a first input 1050 the source of microwave radiation 1001. The source of microwave radiation outputs a phase locked microwave signal for use in the rest of the apparatus. A portion of this signal is diverted (e.g. by a coupler) to a frequency divider 1006 that divides (i.e. reduces) the frequency of the microwave signal, so that it is the same or a similar frequency to that of the first crystal oscillator 1020, and inputs this divided signal to the phase comparator 1015$b$. The phase comparator's output thus depends on the difference in phase between the output of the source of microwave radiation 1001 and the first crystal oscillator 1020. In this way the output frequency of the source of microwave radiation is kept stable as if it increases compared to the first crystal oscillator 1020, the signal sent to the source of microwave radiation's input 1050 is adjusted accordingly causing the microwave radiation output signal to lower in frequency and vice versa. The source of microwave radiation 1001 is also controlled by a signal received at input 1040, which is derived from a second crystal oscillator 1030 which is phase locked to the first crystal oscillator 1020. A portion of the signal from the first crystal oscillator 1020 is input to a second phase comparator 1015$a$ which outputs to the voltage controlled second crystal oscillator 1030, via loop filter 1017. The output of the second crystal oscillator 1030 is sent to a frequency divider 1005, which reduces the signal frequency and outputs to the other input of the phase comparator 1015$a$ in a phase locking arrangement, whereby the output of the second crystal oscillator 1030 is kept stable. It may be preferable to omit frequency divider 1005 and use a VXCO 1030 that outputs a signal centred around the output frequency of TXCO 1020. In this alternative configuration the output from VXCO 1030 is directly fed back to the first input of phase comparator 1015$a$. The second crystal oscillator 1030 also outputs to a second input 1040 of the source of microwave radiation 1040 via a loop filter 1018. In this way, from the two phase locking inputs 1040 and 1050, the frequency of the source of microwave radiation is kept even more stable than if it was phase locked to only one crystal oscillator.

Figure 3:
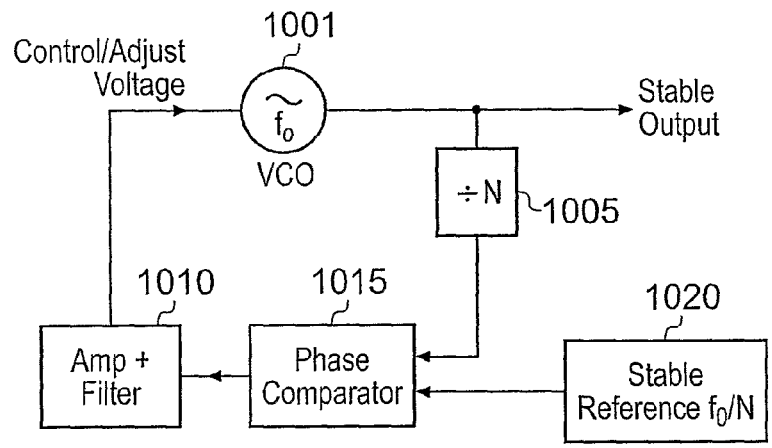
FIG. 3 shows a feedback loop for achieving a stable source of microwave radiation and has already been described.

Instead of phase locking, another approach would be to use a broadband source together with a narrowband filter, as shown in FIG. 3.

Between the source 1 and the probe 5 there are one or more amplifiers 2, an isolator 40 in the form of a circulator for isolating the probe 5 from the amplifiers 2 (to prevent reflected power from damaging the amplifiers), an impedance tuner 50 and a cable assembly 4. The cable assembly 4 has an adjustable length and can be adjusted to give an integral number of quarter wavelengths between the output of the tuner 50 and the end of the probe, this being desirable as it makes it easier to calculate impedance measured at the end of the probe. In this embodiment the impedance tuner is a triple stub tuner and its impedance is varied by movement of three tuning elements in and out of a tuner cavity (as is conventional). The tuning elements are moved by an actuator 1130, which is controlled by a controller 101. The controller may take any suitable form and may be the same as the microprocessor system 101 shown in FIG. 1.

When the apparatus is used to direct microwave radiation through the probe and into tissue 6 at the end of the probe 5, the tissue 6 will reflect a portion of the microwave radiation back through the probe towards the source 1. A directional coupler 200 diverts a portion of this signal to an input B of the detector 100. The reflected signal directed to the detector is indicated by reference numeral 210 in FIG. 5. The detector 100 also takes an input A from a reference signal 255. In this embodiment the reflected signal is taken from a location just after the output of the impedance tuner, it could be taken from other locations (see FIG. 19), but this location is preferred because it generally suffers less noise. In this embodiment the reference signal is derived from the source of microwave radiation 1, being diverted before the amplifier 2 by a directional coupler 250. It would be possible to provide a reference signal by diverting radiation from other locations as is discussed later with reference to the embodiment of FIG. 19. In fact the preferred location is at or just after the output to the tuner 50 as measurements taken from that location suffer less noise generated by other components of the system. For example, amplifier distortion and/or phase shift through amplifier, phase shift through circulator and/or phase shift through tuner. In further alternative embodiments the reference signal 255 may be generated by a separate local oscillator which is independent of the source of microwave radiation 1.

The detector 100 detects the magnitude and phase of both the reflected signal 210 and the reference signal 255. This information is then output to a tissue classifier 150 which classifies the tissue 6 as a particular tissue type (e.g. muscle, fat, cancerous tumour) and outputs the result to a display 160, which displays the tissue type.

The detector 100 may comprise a processor, a vector network analyser, phase comparator and/or a heterodyne detection arrangement comprising one or more mixers and local oscillators. It may also be possible to have two separate detector units for the reference and reflective signals respectively, each outputting to the tissue classifier, rather than a single detector 100 as shown in FIG. 5. One possible configuration of the detector 100 is shown in FIG. 5a. A switch 600 is switchable to take either the signal from input A or input B of the detector. The switch 600 is controlled by signal 610 from controller 101 and can rapidly be switched between the two positions to get up to date information from each signal (i.e. the switch multiplexes the signals). Switch 600 outputs the reflected 210 or reference 255 signal to a mixer 620 where it is mixed with a signal 630 having a frequency different to the frequency of the reference 255 and reflected 210 signals (and therefore usually different to the frequency of the source of microwave radiation 1). The signal 630 may be derived from a local oscillator 640, which is shown as part of the detector 100 in FIG. 5a but which will more usually be from an external source which inputs to the detector 100. In a preferred configuration the mixing down signal 630 is derived from the source of microwave radiation 1 (this is not shown in FIG. 5, but is discussed later with reference to the embodiment of FIGS. 18 and 19). The frequency of the signal 630 is chosen such that it mixes with the reflected signal 210 and reference signal 255 to produce a lower frequency signal which can be output to a digital signal processor 680 (e.g. a vector network analyser or phase comparator). Between the output of the mixer 620 and the digital signal processor 680 there is a low pass filter 640 for eliminating any high frequencies from the mixer, an amplifier 650 and an analogue to digital converter 660. The use of a mixer 620 together with signal 630 to produce an intermediate frequency which can be accepted by the digital signal processor has the advantage that signal accuracy can be maintained and noise levels kept relatively low. An alternative would be to use a frequency divider, but this would introduce more noise into the circuit and so is a less preferred option. The digital signal processor 680 calculates a complex impedance (having both real and imaginary components) on the basis of the input reflected and reference signals. The detector 100 outputs this information to the controller 101 and the tissue classifier 150.

In FIG. 5 the digital signal processor 680 is shown as part of the detector 100 and the tissue classifier 150 is a separate component. However, they could be combined into a single component, for example a dedicated chip, or a program running on a computer, microprocessor or a FPGA, which may contain a logic DSP or microprocessor. In that case this combined functionality component would output to the controller 101.

The tissue classifier 150 classifies the tissue 6 into one of a plurality of different tissue types (e.g. fat, muscle, cancerous tumour) and is also able to detect when the probe is in air and not in contact with tissue on the basis of the complex impedance value output by the detector 100 (in the FIG. 5a embodiment the value output by the digital signal processor 680 which is part of the detector).

The tissue classifier 150 classifies the tissue by comparing the above mentioned complex impedance value (which is representative of the tissue 6 at the end of the probe) with a table of predetermined values assigning complex impedances or ranges thereof to specific tissue types. These predetermined values can be determined empirically or calculated theoretically on the basis of the known impedances of tissue types measured ex-vitro under controlled conditions. Physical properties of tissue; a comprehensive reference book by France A Duck and published by Academic Press London in 1990 (ISBN 0-12-222800-6) provides data from which such theoretical values could be calculated in Chapter 6.

It is expected that ex-vitro measurements of tissue carried out under controlled conditions will differ from values obtained in practice by in vivo measurements, due to blood flow, the nature of the apparatus etc. However, it is expected that there will be a relationship between the theoretical and actually measured values. Thus the tissue classifier may determine the tissue type on the basis of an empirical relationship between a first set of data comprising known or theoretical values from references such as the above mentioned book and a second set of values comprising actual complex impedances measured in practice by the present apparatus or another similar apparatus according to the present invention. Once a few measurements have been made this predetermined relationship can be used in any apparatus.

Before use the apparatus is calibrated by measuring a known impedance at the distal end 5a of the probe (this may for example be air). The measured complex impedance is compared to an expected value (e.g. in the second data set or above-mentioned table) and future measurements are referenced to this calibration measurement. Preferably at least two substances of known complex impedances are used for the calibration (e.g. air and a foam of known complex impedance; the foam surrounding a tip of the probe during calibration).

FIG. 7 shows complex impedance measurements of air, lard, oil, jelly, egg, pork, liver and water (at the end of the probe) made by an apparatus in accordance with the present invention. These materials were stacked together one after the other and in contact with each other. The measurements were taken by inserting the probe sequentially through the materials so that it penetrated them transversely. As the probe reached each material, microwave radiation was injected through the probe, and the complex impedance of that material was calculated from the reference and reflected signals when the distal end of the probe was in that material.

Figure 21:
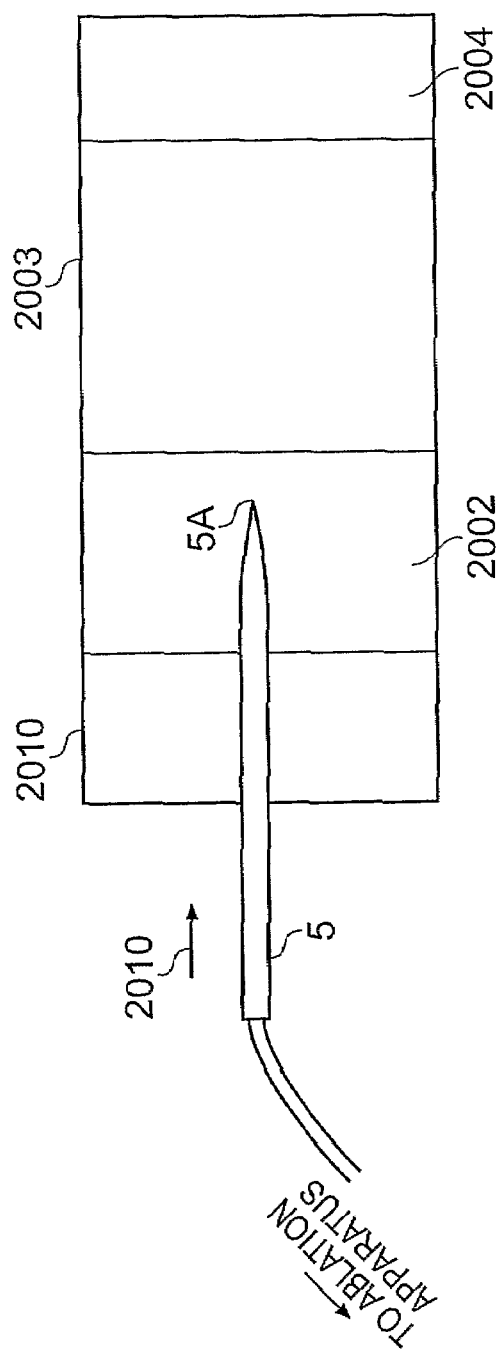
FIG. 21 is a diagram of a probe being inserted into and penetrating sample materials.

FIG. 21 shows an example in which there are four different materials 2001, 2002, 2003 and 2004, stacked together and in contact with each other. The probe 5 is inserted transversely into the materials in direction shown by arrow 2010 so that it penetrates through the materials sequentially. Microwave radiation is delivered to the material at the probe's distal end 5a (e.g. into material 2002 when the probe is in the position shown in FIG. 21) and measurements of that material taken. In this way each material can be measured in turn and the operator can tell from the measurements, what type of material is at the distal end of the probe and whether it is safe and appropriate to ablate or not (e.g. whether or not the distal end of the probe is in cancerous tissue).

In the experiment, it was found that it was still possible to get repeatable impedance measurements for each material type even though they were not isolated from each other. The measurements are given both in the conventional complex impedance format (R+Jxohms), polar coordinates giving the magnitude and phase and Cartesian coordinates as well. The different materials have been split into groups a) containing air, b) containing lard and oil (high in fat), c) containing jelly and d) containing egg white, pork, liver and water. The complex impedances measured of these different groups of substances are widely spaced showing that clear differentiation between them is possible. Two sets of measurements were taken and are shown in tables A and B respectively. The specific values in tables A and B are different because a different tuner setting and different probe were used, but the distribution of the phase is similar, and therefore the differences could be compensated for easily by calibration of the system.

In general, it is necessary to adjust the impedance tuner setting so that the system has optimum phase and amplitude sensitivity (at some tuner settings the detector is able to resolve amplitude, but not phase, other settings are better for phase; the aim is to get a setting which is good for both phase and amplitude measurements). The optimum setting will be different for each probe. Therefore the apparatus has a calibration routine in which the probe is automatically calibrated and the optimum tuner setting determined when the probe is attached to the apparatus. Calibration may be performed by making measurements at different tuner settings against a known load or loads (e.g. air and/or a foam cap placed on the probe).

Figure 8:
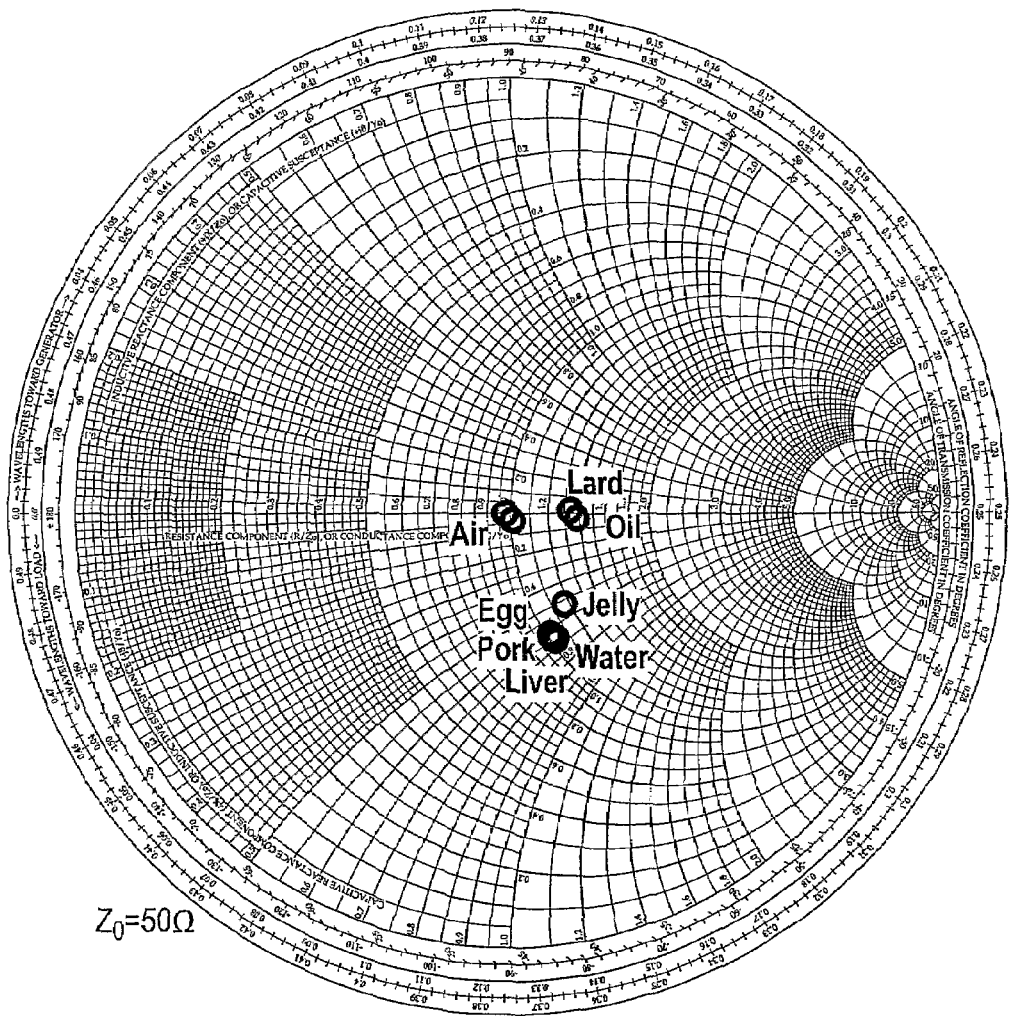
FIG. 8 is a Smith chart showing results from table B of FIG. 7 in graphic form.
Figure 9:
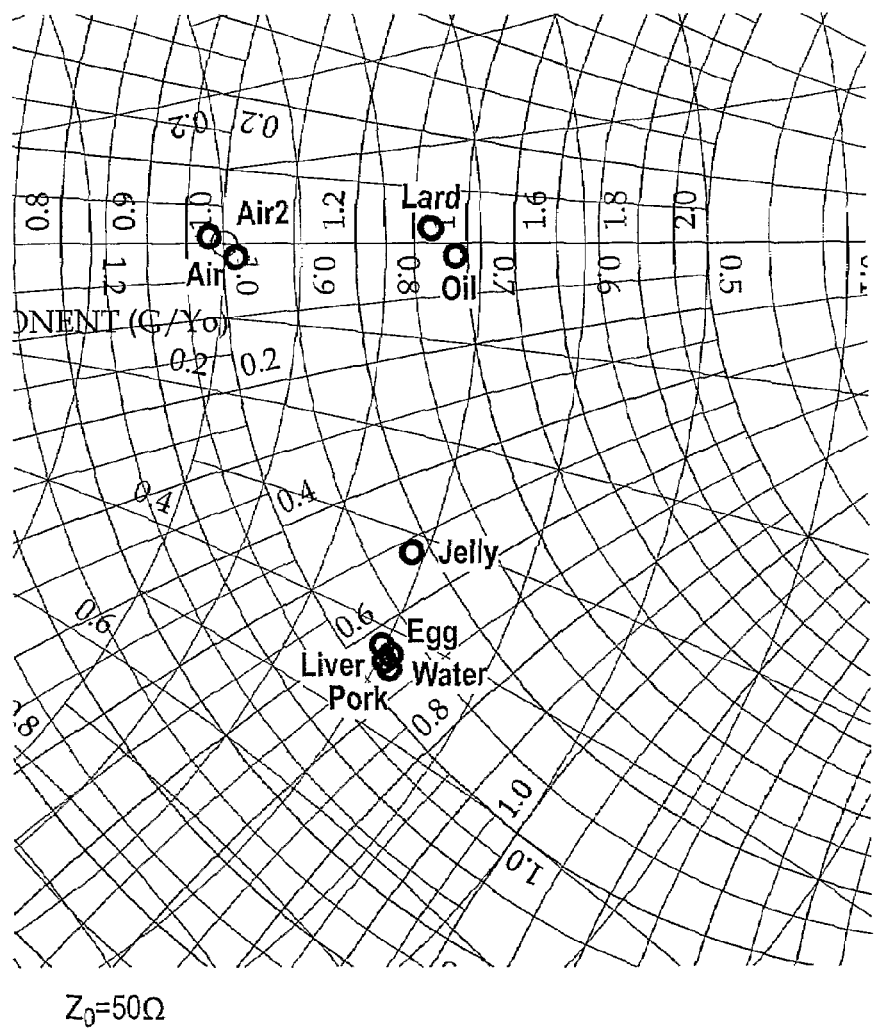
FIG. 9 is an enlarged view of a portion of FIG. 8.
Figure 10:
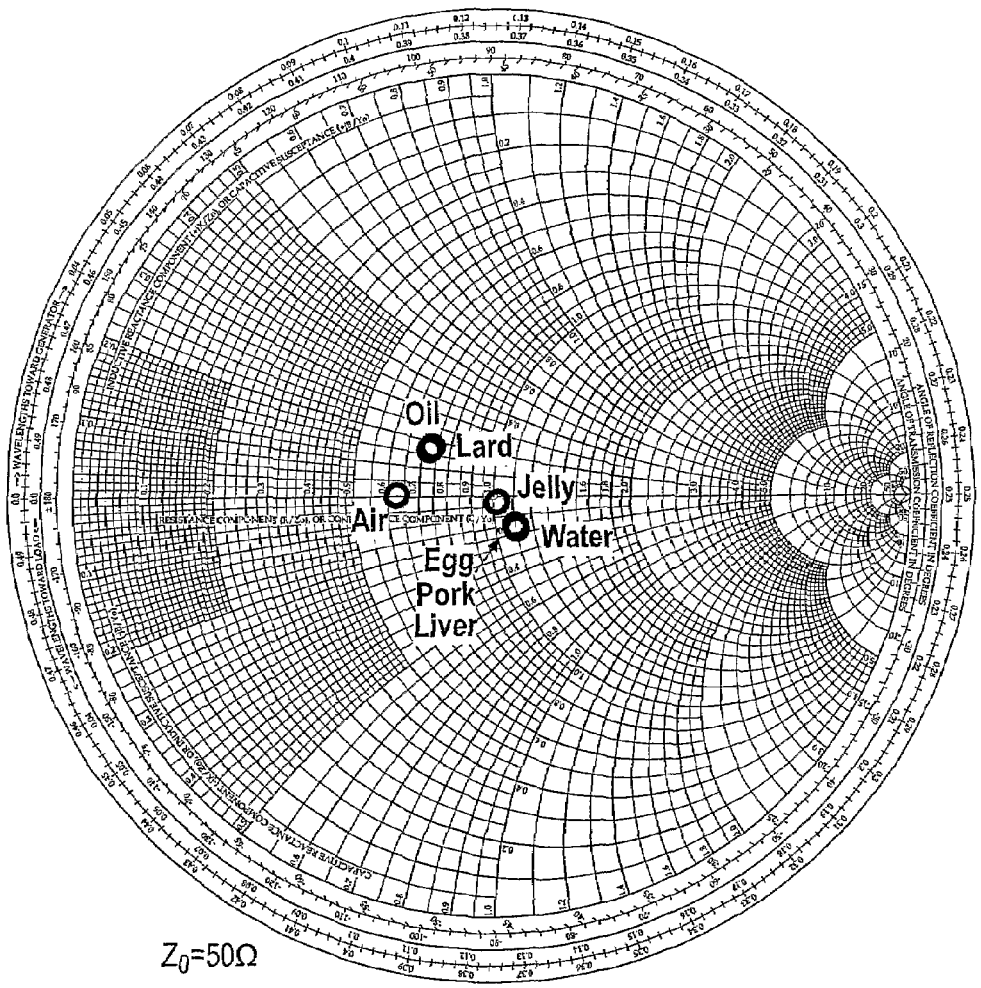
FIG. 10 is a Smith chart showing results from table B of FIG. 7 in graphic form.
Figure 11:
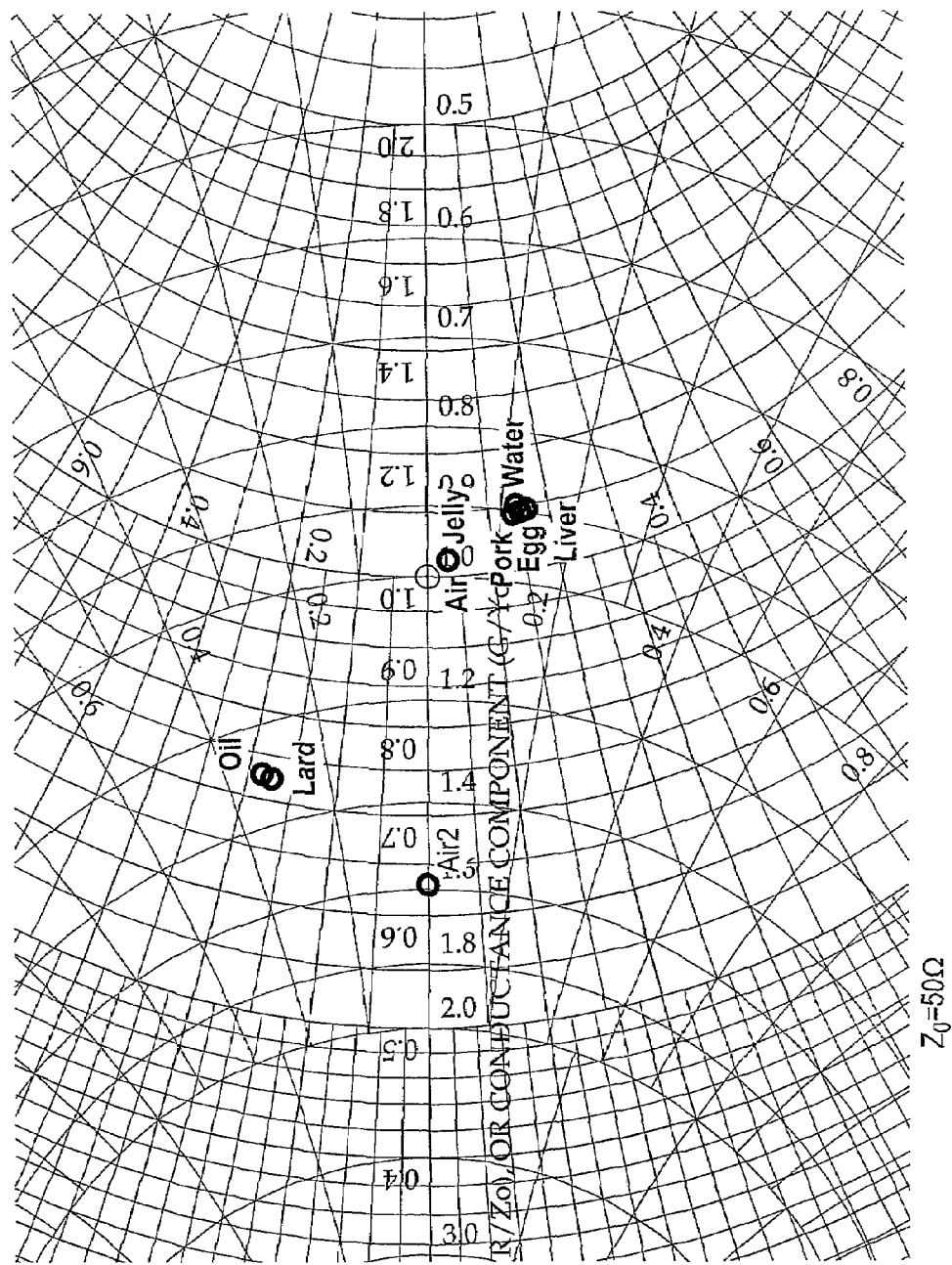
FIG. 11 is an enlarged view of a portion of FIG. 10.

The values of FIG. 7, table A are shown on a Smith chart in FIG. 8. Smith Charts are widely used in microwave engineering. The values on the Smith charts in FIG. 8 are normalised to 50 ohms, but as will be understood by a person skilled in the art, it would be possible to normalise to a different value. It can be seen that the measurements for lard, oil, air, jelly and pork are widely spaced. FIG. 9 is an enlargement of a portion of the Smith chart of FIG. 8 and shows the distribution of the values in group d) more clearly. FIG. 10 shows the measurements of the same substances made using the same apparatus but a different probe and tuner setting. FIG. 10 corresponds to the values in table B of FIG. 7. The values in the Smith chart FIG. 10 are normalised to 50 ohms, but as will be understood to a person skilled in the art, it would be possible to normalise to a different value. As in FIG. 8, a significant difference between the different groups of materials is readily apparent. FIG. 11 is an enlargement of a portion of the Smith chart of FIG. 10.

Figures 12, 13:
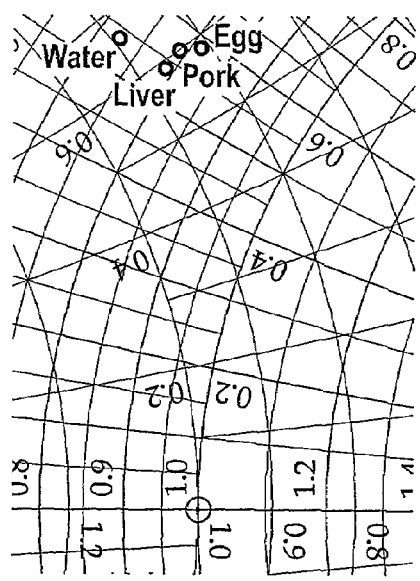
FIG. 12 is another table of results.
FIG. 13 shows a portion of a Smith chart displaying graphically the results of FIG. 12.
Figures 14, 15:
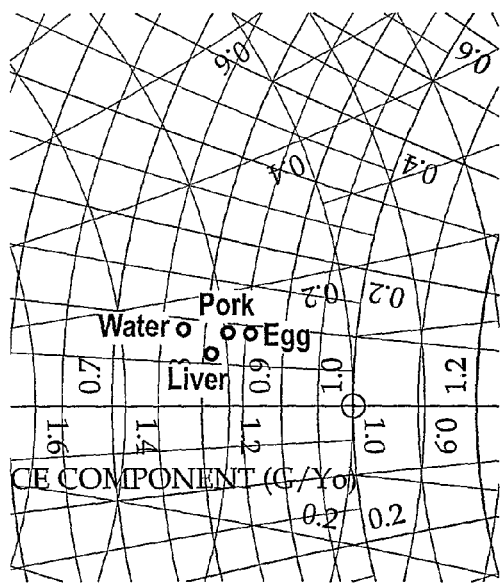
FIG. 14 is another table of results.
FIG. 15 shows a portion of a Smith chart displaying graphically the results of FIG. 14.

FIG. 12. shows a table C giving complex impedance values measured with yet another probe. The format is the same as for the tables of FIG. 7. FIG. 13 is a portion of a Smith chart on which the complex impedance values of FIG. 12 are plotted. It can be seen that the complex impedance values for water, liver, pork and egg are clearly distinguished on this chart. FIG. 14 contains table D which has another set of measurements made with an apparatus according to the present invention. The format is the same as for FIG. 7. FIG. 15 shows a portion of a Smith chart on which the complex impedance values of FIG. 14 are plotted. Again a separation can be seen between the complex impedance values from the chart for water, liver, pork and egg.

Figure 6:
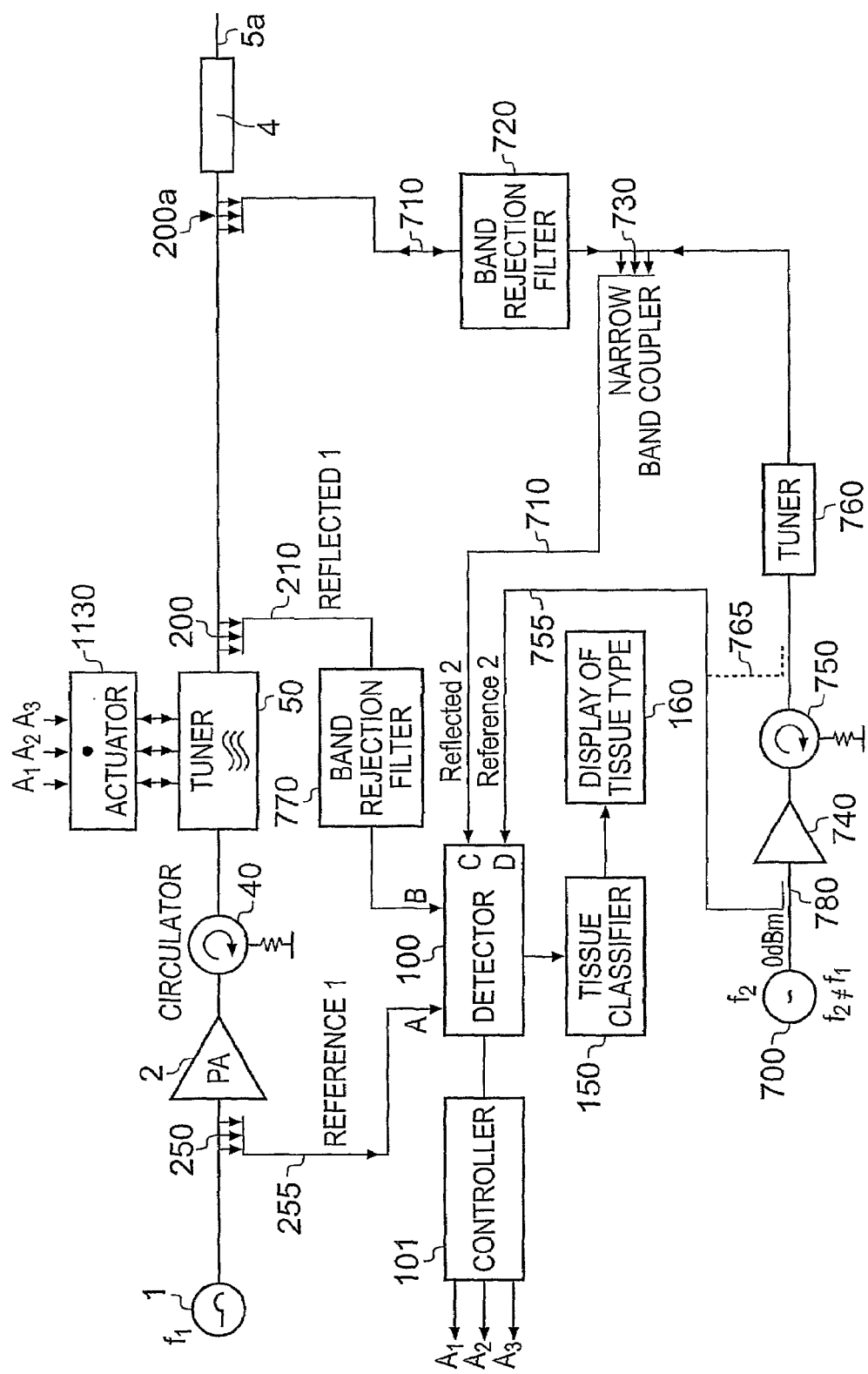
FIG. 6 shows a tissue classification system according to a second embodiment of the present invention.

FIG. 6 shows a second embodiment of the present invention, which is similar to the first embodiment of FIG. 5. Like reference numerals indicate like parts and only the differences will now be described. The main difference is that different frequencies of microwave radiation are used for ablation and tissue measurement/classification.

Thus, there is a second source of microwave radiation 700 having a frequency $f_2$, different to the frequency $f_1$ of the first source of microwave radiation 1. This second source of microwave radiation may be phase locked to a particular frequency. The frequency $f_1$ is used for ablation of tissue. The frequency $f_2$ is used to measure or classify tissue. Generally the second source of microwave radiation 700 will have a relatively low power (compared to first source 1) because it should not ablate tissue, but merely interact with the tissue to provide a measurement.

The signal from the second source of microwave radiation 700 has a frequency of $f_2$ and is amplified by amplifier 740 and then passed through circulator 750 and band filter 730 to probe 4 via a bi-directional coupler 200a. The signal is reflected back through the probe 4 to a third input C of detector 100, via the coupler 200a, band rejection filter 720 and narrow band coupler 730. The narrow band coupler 720 may be a high Q reverse directional coupler. Its purpose is to prevent signals of frequency $f_1$ (from the first source of microwave radiation 1) reaching third and fourth inputs C, D of detector 100.

A forward directional coupler 780 diverts a portion of the signal from the second source of microwave radiation 700 along path 755 to a fourth input D of detector 100. The reflected and reference signals 710, 755 sent to inputs C and D of detector 100 are used to classify the tissue type in the same way as inputs to A and B in the FIG. 5 embodiment. The rest of the circuit is the similar to FIG. 5, except that the radiation from the first source of microwave radiation 1 is used for ablation only and the reference and reflected signals at inputs A and B of detector 100 are used only to determine the appropriate tuning of impedance adjuster 50.

In the primary arrangement shown in FIG. 6 the coupler 780 is positioned between the amplifier 740 and the second source 700. Alternatively a coupler could be positioned near the output of the circulator 750, as shown in the dotted lines 765 in FIG. 6, and used to provide the reference signal 755 to input D; this has the advantage that the signal does not suffer from distortion and phase shift caused by amplifier 740 and additional phase shift caused by the passage of the signal from port one to port two of circulator 750. The circulator 750 prevents reflected signals at the second frequency $f_2$ from feeding back into the amplifier 740 and causing damage to the amplifier's output stage. The coupler 200a acts as a bi-directional element allowing said second frequency to propagate to the distal end of the probe 5a and also to enable the reflection signal from the probe to be detected. A tuner 760 may be provided between the circulator 750 and the band rejection filter 720 in order to allow impedance adjustments, which can optimise the measurement sensitivity of the probe.

It is envisaged that in the FIG. 6 arrangement only one of the sources of microwave radiation 1, 700 will be switched on at any one time. So when first source 1 is switched on the apparatus is in ablation mode; and when second source 700 switched on, the apparatus is in measurement or tissue classification mode. It would however be possible to have the second source 700 switched on at all times in order to allow measurement to be carried out continuously, even when ablation was being carried out. In that case it would be desirable to have a band rejection filter 770, configured for preventing the passage of frequency $f_2$, positioned between the output of tuner 50 and the second input B of detector 100 in order to prevent frequency $f_2$ from reaching input B.

It is of course also possible to have an ablation and tissue classification apparatus with a single source of microwave radiation and a variable amplifier or attenuator used to vary the signal amplitude between tissue classification levels. However, the FIG. 6 embodiment has the advantage that different frequencies can be used for tissue ablation and tissue classification. This makes it possible to select a particular frequency for tissue classification which will give optimum response due to the characteristics of the tissue being looked for (some tissues will give a peak response at certain frequencies). It also makes it possible to carry out ablation and classification simultaneously as different frequencies are used for each.

Figure 18:
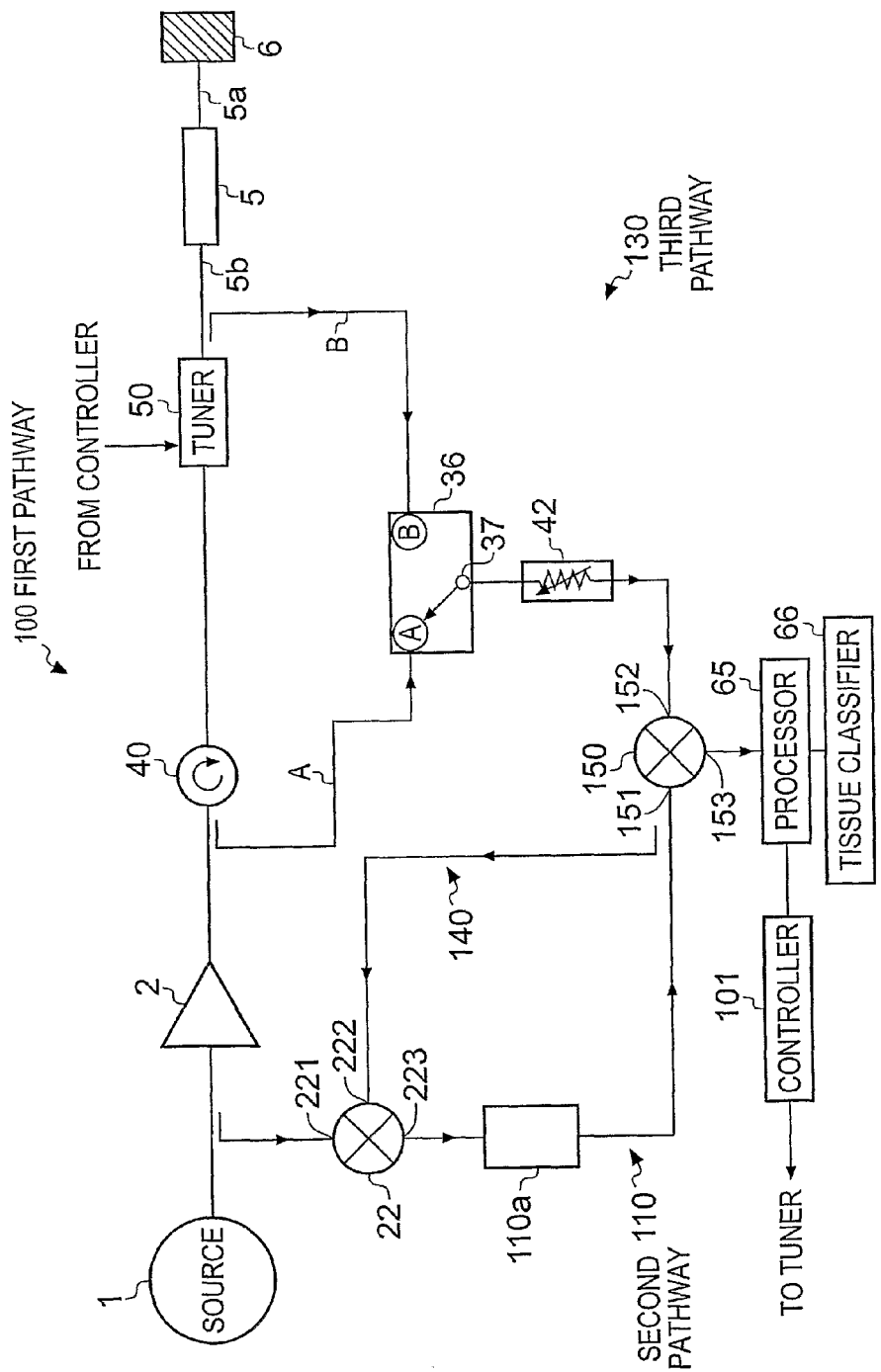
FIG. 18 is a simplified diagram of an ablation and tissue characterisation apparatus according to the an embodiment of the present invention.
Figure 19:
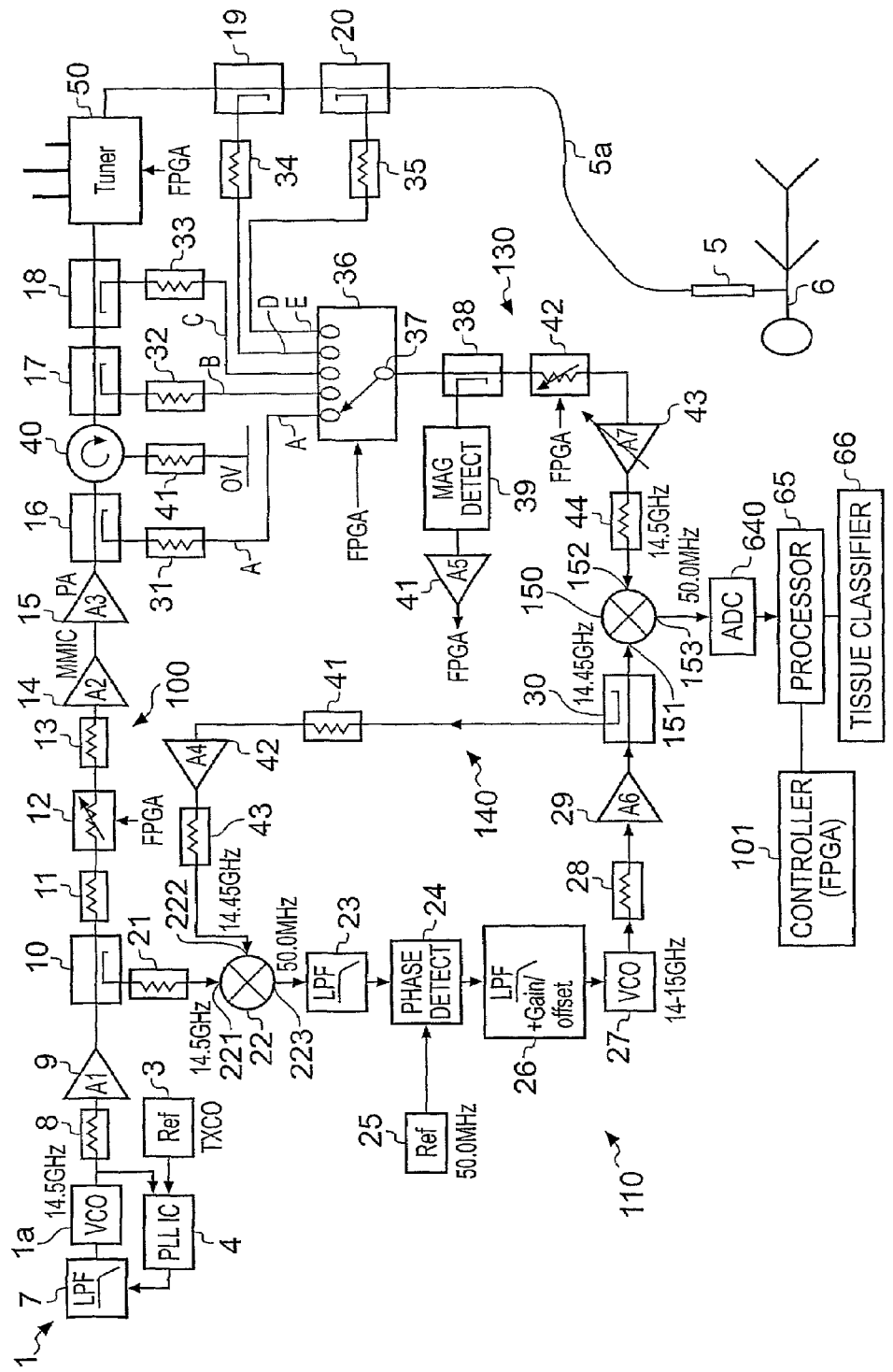
FIG. 19 is a more detailed system diagram of an embodiment of the present invention.

The tissue classification system of FIGS. 18 and 19 may also act as a tissue ablation system as well as a tissue classification system.

In that case the apparatus has a tissue classification mode and a tissue ablation mode. In the tissue ablation mode a signal having sufficient amplitude to ablate the tissue is directed through the probe 5, and the controller 101 and actuator 1130 are used to dynamically match the impedance of the apparatus to the tissue 6 being ablated so that energy reflection back into the system is minimised. In the tissue classification mode a lower power signal is directed through the probe 5 and the impedance of the impedance tuner 50 is fixed to provide a stable reference point against which the complex impedance measurements can be taken. The apparatus may be switched quickly back and forth between the tissue ablation and tissue classification modes. Any suitable actuation method may be used for actuating the tuner, for example linear motors, moving coil arrangements, stepper motors, piezo electric actuators or magnetostrictive actuators. This list is not exhaustive and other possibilities will be apparent to a person skilled in the art. Magnetostrictive actuation is in itself inventive and this will now be discussed in more detail.

Figure 16:
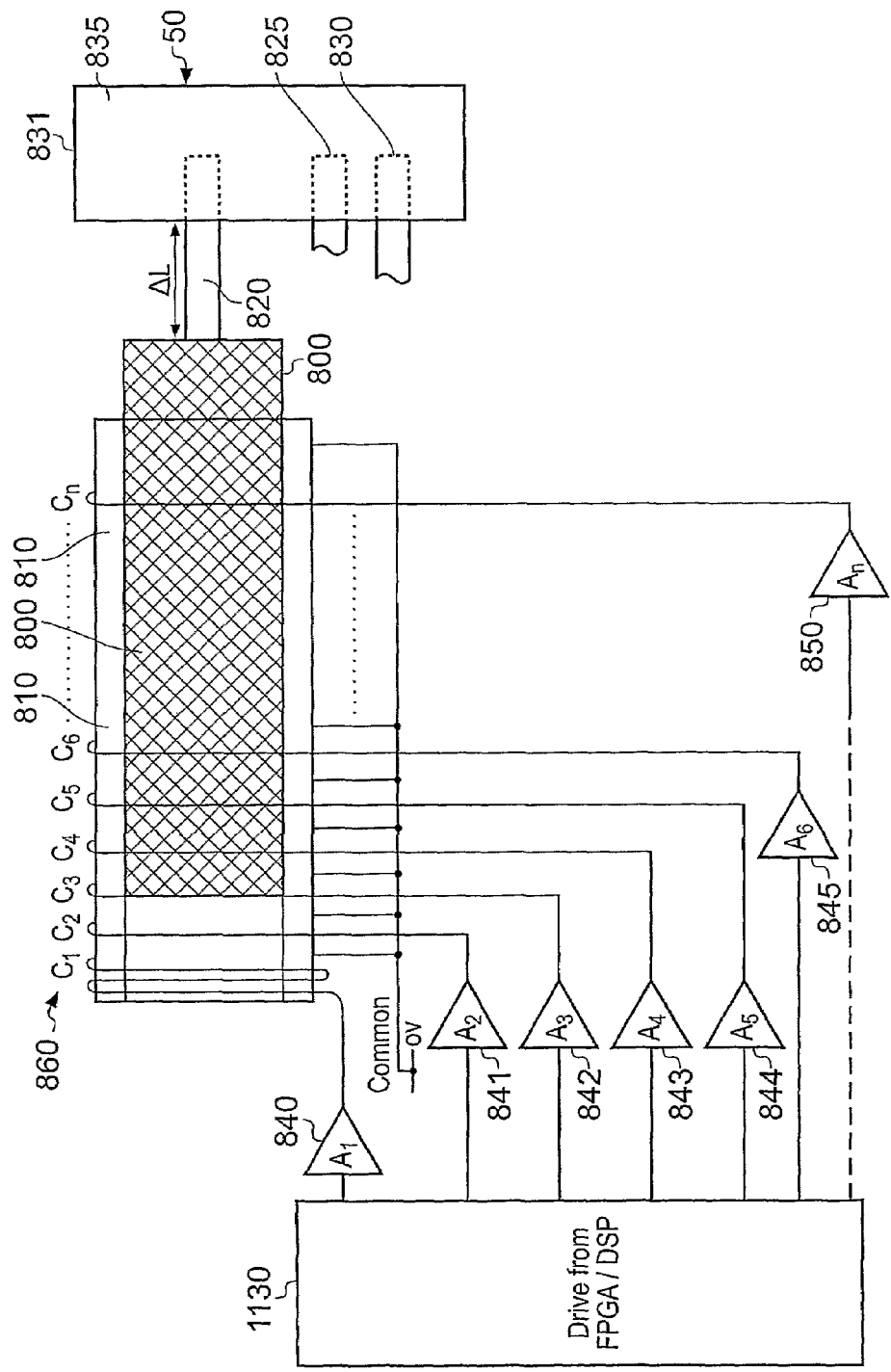
FIG. 16 is a schematic diagram showing a tuner and actuation arrangement according to a third embodiment of the present invention, and FIGS. 17($a$) to ($e$) illustrate movement of the magnetostrictive actuator of FIG. 12 in its housing.

FIG. 16 shows an actuation system for an impedance tuner which could be used with the tissue classification system and/or ablation system described above or in any apparatus which requires actuation of an impedance tuner for microwave radiation. It may be used in a medical apparatus or a non-medical apparatus.

The impedance tuner shown in FIG. 16 is a triple stub tuner and comprises an enclosure 831 containing a tuning cavity 835 in to which three tuning rods 820, 825, 830 are extendable to variable degrees. The tuning rods 820, 825, 830 are made from brass in this embodiment, other suitable materials will be apparent to a person skilled in the art. The complex impedance of the impedance tuner 50 is varied by varying the degree to which any or all of the tuning rods 820, 825, 830 extend into the tuning cavity 835. It will be apparent to a person skilled in the art, that the actuation system can be applied not only to triple stub tuners, but also to other types of impedance tuners having actuatable elements.

The actuation system comprises a rod of magnetostrictive material 800, which is positioned at least partially inside a housing 810 and one end of which is coupled to one of the tuning rods 820. The magnetostrictive rod 800 is preferably made from terfenol-D. The housing 810 is made from a non-magnetic metal material or plastics material; it has an internal bore which receives and forms a tight interference fit with the magnetostrictive rod 800.

There are a plurality of current windings, $C_1$ to $C_n$ (only the first six and last of these being shown in FIG. 13), generally indicated by reference numeral 860, around the exterior of the housing 810 and the magnetostrictive rod 800. Each set of current windings $C_1$, $C_2$ etc is connected to a respective current source 840, 841, 842, 843, 844, 845 . . . 850. In this embodiment the current sources take the form of fast amplifiers, which are controlled by the actuation controller 1130. The actuation controller 1130 may take the form of a FPGA or any electronic hardware configured or programmed to effect suitable actuation of the magnetostrictive rod 800 via the restrictive current sources.

Although not shown in FIG. 15, the other rods 825 and 830 are each coupled to their own respective actuation systems which are identical to the system described above and below for tuning rod 820.

In use, the controller 1130 causes the current sources to pulse the current through one or more of the respective coil windings 860. These current pulses through the windings generate a magnetic field causing the magnetostrictive material in the rod 800 to expand longitudinally, and consequently the tuning rod 820 can be moved further in to the tuning cavity 835. The other tuning rods 852 and 830 are also controlled in a similar fashion by respective current sources linked to the controller 1130, but for clarity this is not shown in FIG. 16.

An advantage of having a separate current source for each winding $C_1$, $C_2$, etc is that the rate of change of current is limited and so the response time us kept short, also by having a small number of windings for each current source the inductance is kept small and so it is possible to switch current through the coils faster and the induced voltage is limited.

The housing 810 forms a tight interference grip with the magnetostrictive rod 800, but the rod 800 is able to move within the housing when a current (magnetic) pulse causes it to expand. Thus, the magnetostrictive rod 800 is able to "crawl" forwards and backwards within the housing and this is explained with reference to FIGS. 17(a) to 17(e).

Figure 17:
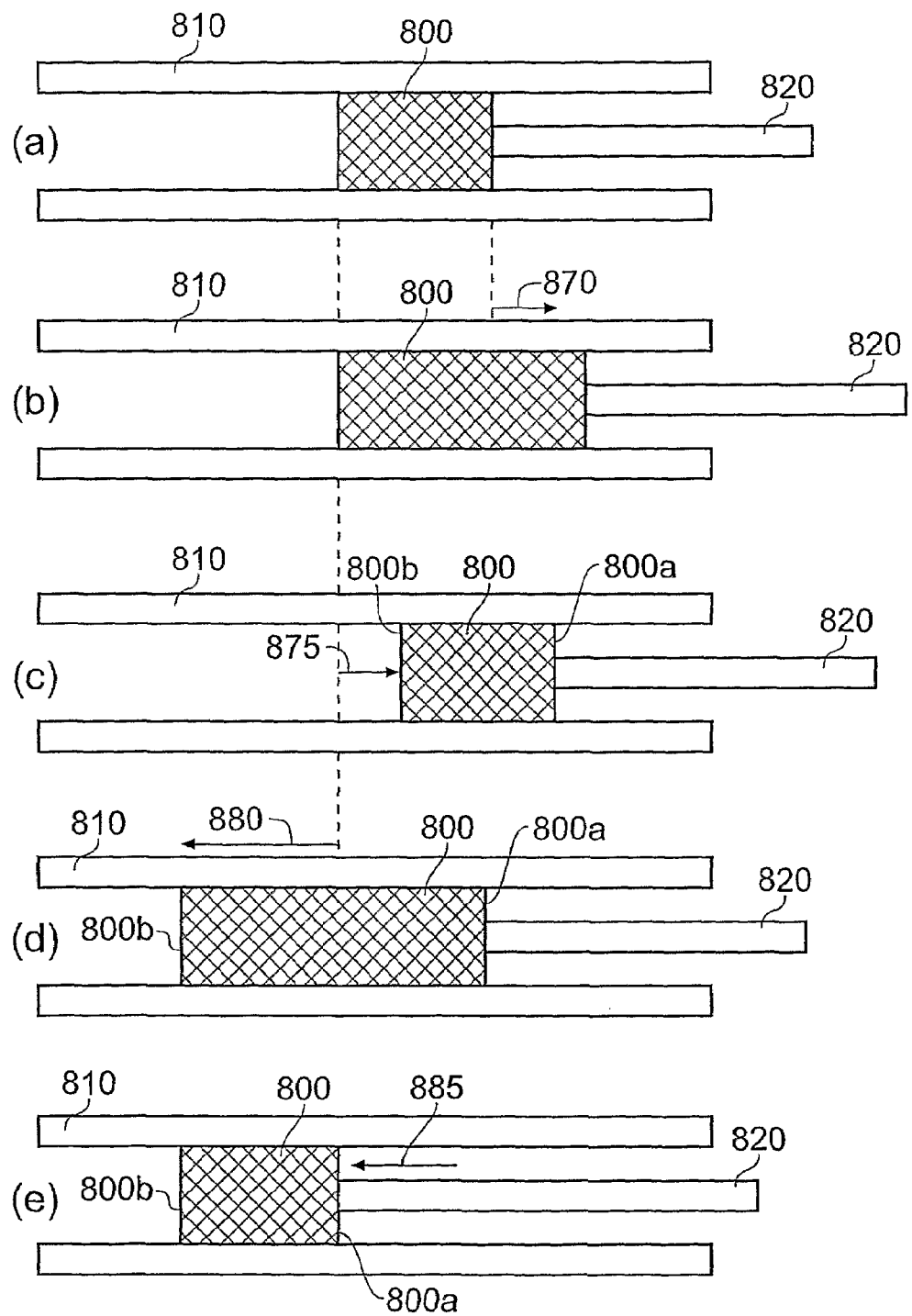

The magnetostrictive rod 800 is shown in an initial position in the housing 810 in FIG. 17(*a*). The tuning element 820 is mounted on the end of the magnetostrictive rod 800 as in FIG. 16. FIG. 17(*b*) shows the situation when a current pulse through one or more of the windings 860 surrounding the magnetostrictive rod 800 produces a magnetic field causing it to expand in the direction shown by arrow 870. The tuning rod 820 is therefore pushed further into the tuning cavity 835 (not shown in FIG. 17). FIG. 17(*c*) shows the situation after the pulse has passed and the magnetostrictive material 800 relaxes back to its former length. The front of the rod 800*a* is tightly gripped by the housing 810. The grip at this end of the rod is tighter than that at the back end 800*b* because the rod has just expanded in this direction. Therefore when the magnetostrictive rod 800 resumes its original length the back of the rod 800*b* moves forward towards to tuner end of the housing 810 as shown by arrow 875. Thus the magnetostrictive rod 800 is moved forward within the housing 810. By continuing this process it is possible to effect a large degree of movement of the tuning rod 820 even if the magnetostrictive rod 800 (the actuator) is relatively short.

By reversing the polarity of the current pulses (and therefore reversing the polarity of the magnetic field produced), it is possible to get the magnetostrictive rod 800 to expand in the opposite direction. This is shown in FIG. 17(*d*). In this case it is the rear end 800*b* of the rod 800 which moves backwards in the housing 810 away from the tuner 50, in the direction shown by arrow 880, when the magnetic field is applied. Subsequently, once the pulse has passed, the magnetostrictive rod 800 relaxes to its former length and as the rear end 800*b* is tightly gripped it is the front end 800*a* which moves backwards in the housing 810 away from the tuner 50 in the direction shown by arrow 885. In this way the length of the tuning rod 820 extending into the tuning cavity 835 can be reduced. By repeating this operation it is possible to move the tuning rod 820 a relatively large distance even if the length of the magnetostrictive element 800 itself is relatively small.

It will be appreciated by a person skilled in the art that the actuation method described above can be applied not only to triple stub tuners, but also to double or single stub tuners, phase shifters and other types of impedance tuner, especially impedance tuners which have one or more actuatable elements which are moved linearly in order to vary the impedance.

Another embodiment of the present invention will now be described with reference to FIGS. 18 and 19. This is similar to the embodiment of FIG. 5 except that the mixing down signal is derived from the source of microwave radiation. There are also some more complex additions to the circuitry, which provide a greater variety of reflected and reference signals, on the basis of which to calculate the complex impedance of tissue, and other components for allowing the apparatus to operate efficiently in both tissue classification and tissue ablation modes.

Figure 4:
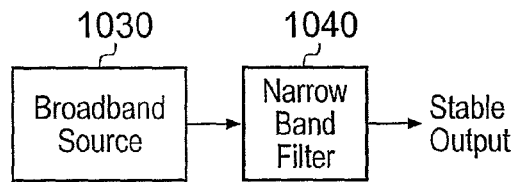
FIG. 4 shows an alternative configuration for achieving a stable source of microwave radiation and has already been described.
Figure 2:
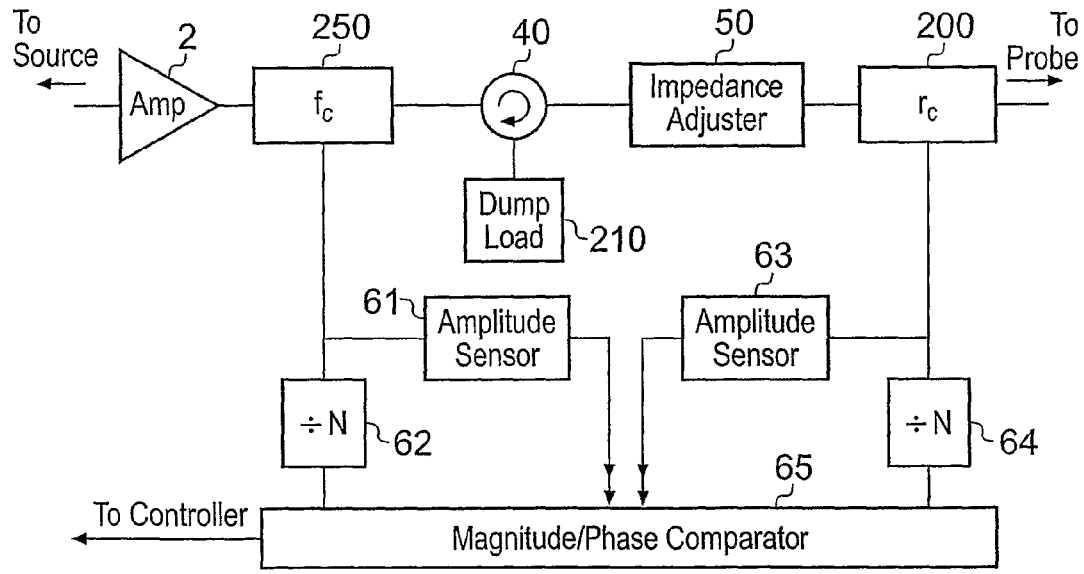
FIG. 2 shows an alternative detection arrangement having a phase comparator, for use with an ablation apparatus such as that shown in FIG. 1 and has already been described.

FIG. 18 is a simplified system diagram of a tissue ablation and classification apparatus according to this embodiment of the present invention. The apparatus comprises a stable source of microwave radiation 1 connected to a probe 5 along a first pathway 100. The source may, for example be as any one described previously and shown in FIG. 3, 4 or 5. The pathway has an amplifier circuit 2, circulator 40 and impedance tuner 50 in that order between the source and the probe 5. The distal end of the probe 5*a* can be inserted into tissue 6, which is to be classified or ablated. The probe 5 has a flexible cable assembly 5*b* for attachment to the rest of the apparatus, e.g. the impedance tuner 50. A second pathway 110 is coupled to the source 1 and delivers the signal to a first input 151 of a first mixer 150. The second pathway 110 has various electronic components indicated generally by box 110*a*. A third pathway 130 conveys a portion of forward and/or reflected microwave radiation which has been diverted from the second pathway, to the second input 152 of mixer 150. Forward directed radiation is radiation travelling from said source to said probe 5, reflected radiation is radiation reflected by the tissue 6 back through the probe 5. As the microwave frequencies input into the first 151 and second 152 inputs of mixer 150 differ, the resultant frequency from the output 153 of the first mixer 150 will be in a lower, e.g. in the MHz range which can be accepted by digital processor 65 connected to the output of the first mixer 150, e.g. 10 to 250 MHz. Processor 65 is capable of determining both the magnitude and phase of the input signal and corresponds generally to detector 100 of the FIG. 5 embodiment. Information relating to the magnitude and phase of the input signals can be used by controller 101 to determine an appropriate adjustment of the complex impedance of the impedance tuner 50 to match the impedance of the apparatus to that of the tissue 6 being ablated, when the apparatus is in ablation mode.

A phase locked loop is formed on the second pathway between the source and the first mixer, to lock the frequency of the signal input to the first mixer to that of the source 1. This loop comprises a second mixer 22 having a first input 221 coupled to the source of microwave radiation 1 and an output 223 to a forward path of a phase locked loop leading to the first input 151 of first mixer 150. A feedback path of the phase locked loop is formed by a fourth pathway 140 which diverts a portion of the radiation from the first input 151 of the first mixer to the second input 222 of the second mixer. The phase lock loop is described in more detail later.

Reflected radiation travels through the probe 5 and down a third pathway 130, including channels A and B, switch box 36 and variable attenuator 42 (and/or for a variable gain amplifier not shown in FIG. 18) to the second input 152 of the first mixer 150.

The third pathway includes two separate channels A and B in a first portion, which leads from the first pathway to a switchbox 36. Channel A channels forward directed radiation from the first pathway 100 to switch box 36 (in this example the radiation is picked up before the circulator 40). Forward directed radiation could also be measured after the circulator and before the tuner or after the tuner; after the tuner is the preferred location. The switch box 36 is controlled by controller 101 to direct either the forward directed radiation from path A or the reflected radiation B through switch box output 37, via the variable attenuator 42, to second input 152 of the first mixer 150 (e.g. by time multiplexing so the processor 65 can receive information from both). By using information from both these pathways, pathway A in effect provides a reference signal to compare the reflected signal pathway B against, and the tissue classifier 66 can classify the tissue 6 into one of a plurality of tissue types. Whether the radiation sent to the second input 152 is forward directed or reflected radiation, it is mixed with the signal from the second pathway 110 so that the output signal 153 is at a lower frequency readable by the processor 65 via an ADC (not shown in FIG. 3). The variable attenuator 42 (and/or a variable gain amplifier not shown in FIG. 3) is controlled to a level acceptable by the first mixer 150 where necessary.

The apparatus will now be described in more detail with reference to FIG. 19.

In this embodiment the source of microwave radiation 1 comprises a voltage controlled oscillator controlled by a phase locked loop including a local oscillator 3, a phase locked loop integrated circuit 4 and a loop filter 7. The phase locked loop is employed to provide a stable output frequency from the voltage controlled oscillator 1*a*. In this embodiment the voltage controlled oscillator (VCO) is controlled to output a fixed frequency of 14.5 GHz, but it will be understood by a person skilled in the art that other microwave frequencies could be chosen or that the phase locked loop and VCO may be tuneable to provide a different frequency. Radiation from the source of microwave radiation 1 is sent along a first pathway 100 to probe 5 where it is directed into a patient having tissue 6. Along the first pathway there is a first attenuator 8, a first preamplifier 9, a forward coupler 10, a second attenuator 11, a variable gain amplifier 12, a third attenuator 13, a second preamplifier 14 and a power amplifier 15. This makes up an amplification part of the system. Also on the first pathway, between the aforementioned amplification components and the probe 5 are an isolating device 40 (e.g. a circulator) and an impedance tuner 50 having a variable complex impedance. The isolating device 40 acts to prevent reflected radiation from entering the amplification part of the circuit and redirects any reflected radiation to a dump load 41. The impedance-tuner 50 has an impedance which can be varied by controller 101 on the basis of the signal received from the mixer 150 and processed by the processor 65. The controller 101 is configured to control the impedance tuner 50 so that the complex impedance of the apparatus matches that of the tissue 6 being ablated. This impedance matching can be carried out dynamically to minimise reflection of energy even when the complex impedance of the tissue 6 changes.

The second pathway 110 will now be described. The second pathway 110 is between a second mixer 22 and a first mixer 150. The second mixer 22 has a first input 221 which is coupled to the source of microwave radiation 1 via said first forward directed coupler 10 and a attenuator 21. The mixer 22 also has a second input 222 and an output 223. The apparatus is configured so that the frequency input into the second input 222 will generally be different; in this embodiment 14.45 GHz is given as an example, to the frequency of the source of microwave radiation. As a result, a lower frequency, in this embodiment 50 MHz, is output from the output 223 of the second mixer along a forward path 110 of a phase locked loop which leads to first input 151 of first mixer 150.

The signal from output 223 of the second mixer 22 is passed through a low pass filter 23 to remove any high frequency components from the mixing process e.g. the sum frequency. The signal then passes to the input of a phase detector 24. The phase detector may, for example be an EXOR gate, but other possibilities will be apparent to a person skilled in the art. The phase detector 24 compares the phase of the input signal with that of a stable local oscillator 25. The local oscillator 25 in this embodiment is a temperature compensated crystal oscillator with low drift (e.g. 1 pmm with temperature); in this embodiment its frequency is 50 MHz, but other frequencies could be used. The phase detector 24 outputs a control signal to a voltage controlled oscillator 27 via a loop filter 26 and DC offset adjuster. The loop filter and DC offset adjuster adjusts the output of the voltage controlled oscillator 27 and may add and/or offset the input voltage to VCO 27, where necessary to provide a signal which can be used to control the voltage controlled oscillator 27. The control signal is such that the voltage controlled oscillator 27 adjusts its output on the basis of the phase difference between the stable crystal oscillator 25 and the output of the mixer 22, to produce a desired frequency from the voltage controlled oscillator 27. The voltage controlled oscillator's output is output via attenuator 28 and amplifier 29 to first input 151 of first mixer 150. Some of the signal sent to the first input 151 is diverted by coupler 30 along a feed back path 140 which leads to the second input 222 of the second mixer 22. The feed back path 140 has an attenuator 41, amplifier 42 and attenuator 43 between the coupler 30 and the second mixer 22.

As the signal input to the first input 151 of the first mixer 150 is locked to the source of microwave radiation 1, any change in frequency in the source will cause a change in the frequency input to the first input of said first mixer and so the difference between the two and therefore the intermediate frequency output from the mixer will be constant.

The third pathway 130 comprises a plurality of channels A, B, C, D and E leading from respective forward and reverse directed couplers 16, 17, 18, 19 and 20 on the first pathway to respective terminals of a switching device 36 and a path from the switching device to the second input 152 of the first mixer 150. Each pathway A to E has a respective attenuator 31, 32, 33, 34, 35. The switching device 36 is controlled by the controller 101 to direct a signal from one of the channels A to E through output 37 toward second input 152 of the first mixer 150. Couplers 16, 17 and 19 are forward couplers and so channels A, B and D channel forward directed radiation from the first pathway to the switching device 36. Couplers 18 and 20 are reverse couplers and channels C and E channel reflected radiation to the switching device 36. Usually controller 101 will control the switching device 36 to sequence through inputs A to E in turn so that one signal at a time can be analysed (i.e. time multiplexing). A FPGA is preferred, as the processor 65 is due to the first response required to switch between channels and make the phase measurements. The forward directed radiation channels provide reference signals, which can be used together with one or more reflected radiation signals from the reflected radiation channels to determine the complex impedance of the load or tissue at the end of the distal end of the probe and/or to classify the tissue; this is discussed in more detail a bit later.

The signal sent through output 37 of the switching device 36 passes through a coupler 38, a variable attenuator 42, variable amplifier 43 and (fixed value) attenuator 44 before reaching second input 152 of the first mixer 150. The coupler 38 directs a portion of the signal to a magnitude (amplitude) detector 39, which then outputs a control signal to the controller 101 for controlling the level of attenuation or the level of amplification of variable attenuator 42 or variable amplifier 43. The control signal may be sent to controller 101 via a buffer amplifier 41. The control signal may simply be information relating to the detected magnitude. The controller 101 then controls the attenuation of the variable attenuator 42 or gain of the variable amplifier 43, on the basis of said control signal from the amplitude detector 39, so that the signal input to second input 152 of mixer 150 is within a predetermined power band which can be accepted by the first mixer 150. This is necessary, because otherwise the signal input to the first mixer could vary widely between when the apparatus is used in an ablation mode (high power, low attenuation at amplifier 12) and tissue classification mode (low power). As the attenuator 42 is a continuously variable, the output signal can be kept at a fixed power if necessary.

An analogue to digital converter 640 is provided between the output 153 of the first mixer 150 and the processor 65. Processor 65 is configured to determine the complex impedance of the tissue 6 on the basis of the input signals (from pathways A to E and first mixer 150). It then communicates this information to controller 101, which controls the impedance tuner 50 and/or other elements of the circuit on the basis of this information. The processor 65 also outputs this information to tissue classifier 66, which uses the detected complex impedance to classify the tissue into a tissue type; preferably the tissue classifier 66 is part of the processor 65. While processor 65, controller 101 and tissue classifier 66 have been shown as separate components in FIGS. 3 and 4 it will be understood that they can be combined into a single component, for example a program running on a computer, microprocessor or a FPGA, which may contain a logic DSP or microprocessor.

More specifically, the tissue classifier 66 classifies the tissue 6 into one of a plurality of different tissue types (e.g. fat, muscle, cancerous tumour) and is also able to detect when the probe is in air and not in contact with tissue on the basis of the complex impedance value output by the processor 65.

In a preferred configuration the processor 65 calculates a complex impedance value which is representative of the tissue 6 at the end of the probe, on the basis of the amplitude and phase of the reference signals (channel A, B or D) and reflected signals (channels C or E); and the tissue classifier 66 classifies the tissue 6 at the end of the probe by comparing this calculated complex impedance value with a table of predetermined values assigning complex impedances or ranges thereof to specific tissue types. While only one reference and one reflected signal is needed, the introduction of more channels enables the complex impedance characteristics of the apparatus to be measured and so this information can be used to provide more accurate tissue measurement and classification information. The predetermined values can be determined empirically or calculated theoretically on the basis of the known impedances of tissue types measured ex-vitro under controlled conditions. Physical properties of tissue; a comprehensive reference book by Francis A Duck and published by Academic Press London in 1990 (ISBN 0-12-222800-6) provides data from which such theoretical values could be calculated in Chapter 6. The tissue classification on the basis of the detected complex impedance is the same as classification described above with reference to FIGS. 5 to 15.

A possible configuration of the probe assembly 5, 5a will now be described in more detail. It is to be understood that any probe capable of delivering radiation to the tissue and receiving the reflected radiation can be used with the present invention. In addition the probe should be capable of being inserted into tissue (either directly or via a tube). Therefore, the following arrangements are given by way of example only, and are not intended to limit the present invention. Alternative arrangements will be apparent to a person skilled in the art and still within the scope of the appended claims.

FIG. 22(a) illustrates a preferred structure for the probe 5. The probe 5 is coaxial. It has an outer jacket or casing 505, preferably made from stainless steel, to provide rigidity to enable the probe to be pushed through tissue layers without the need for a trocar or insertion tube. In this example, the diameter 510 of the outer jacket 505 is 3 mm or less (8 French or lower), and the length between 20 mm and 200 mm; preferably 120 mm. In this embodiment the outer jacket is made of metal and acts as the outer conductor. The inner conductor is made from any appropriate material, e.g. stainless steel, silver coated stainless steel or silver coated copper. A dielectric 530, separates the inner conductor 515 from the outer conductor 505. Preferably the dielectric is a low loss material (at the GHz frequency). The dielectric 530 is used to ensure that a fixed characteristic impedance (e.g. 50Ω) is maintained throughout the co-axial structure and to ensure that the inner and outer conductors cannot be shorted together. The value of characteristic impedance is governed by the ratio of the inner diameter 510 of the outer conductor 505 and the outer diameter 525 of the inner conductor 515, and the value of relative permittivity of the dielectric material 530 between said conductors. The dielectric material 530 also increases the voltage breakdown capability of the structure. It is preferable to use a low loss dielectric material with a low relative permittivity; suitable materials include: low density PTFE, expanded PTFE and tape wrapped PTFE.

A cone 520 is fitted to the distal end of the probe. This allows the probe to be pushed through the tissue layers with relative ease. The cone 520 is made from a rigid dielectric material that has a low loss factor at 14.5 GHz. Suitable materials for the cone include microwave ceramics, in this example a high temperature, low loss plastic known as ECCOSTOCK HiK500F, available from Emerson and Cumming Microwave Products is used. Preferably the cone material exhibits a relative permittivity of between 3 and 30.

In the embodiment shown in FIG. 22, the inner conductor 515 protrudes through the end of the cone 520. This feature is especially advantageous where the invention is to be used for both treatment and measurement since it has been found that exposure of the inner conductor provides optimal measurement sensitivity. Other possible configurations include: an inner conductor formed as an H-field loop inside cone and inner conductor fully inside cone.

The cone 520 and the end of the outer jacket 505 are coated to prevent ingress of fluid or tissue inside the probe. The coating may be any suitable material, Parylene C material is used in this embodiment.

The probe 5 is connected to a co-axial cable 540 assembly using a connector 535, e.g. an SMA series microwave connector, as shown in FIG. 22 (b). Alternatively the probe 5 may be integrated to a cable assembly, as shown in FIG. 22(c). FIG. 22 (a) is an enlarged and detailed view of the parts of FIGS. 22(b) and 22(c) which are ringed in dotted lines.

It would also be possible to use a semi-rigid probe instead of the rigid probe described above. Such probes can be inserted down an endoscope tube, a cannula, a trocar or other tube inserted through the body. In some cases they may also be inserted directly into the biological system or through tissue that presents no, or very little, physical resistance. The details are similar to those described above except the probe is not so rigid and thus different materials may be used, for example the outer jacket could be made from aluminium, the inner conductor from silver coated copper wire and the dielectric from tape wrapped T-PTFE.

Typical applications for the apparatus described in this application include the treatment and detection of breast, brain and liver tumours. It can also be used for certain heart procedures and detection and treatment of Desmoid tumours (benign fibrous neoplasms originating from the musculoaponeurotic structures throughout the body). Other possibilities will be apparent to a person skilled in the art.

The invention claimed is:

1. A tissue classifying apparatus comprising:
   a microwave radiation source which outputs microwave radiation having a single stable frequency in the range of 5 to 60 GHz;
   a cable having a high phase stability under flexure which connects at a first end to the microwave radiation source;
   a probe which is connected to a second end of the cable, which is fitted with a distal end made from a rigid low loss ceramic which distal end penetrates into biological tissue to deliver the microwave radiation from the microwave radiation source to a region of tissue in direct contact with the distal end of the probe and which produces a reflected signal from the microwave radiation reflected back from the region of the tissue in direct contact with the distal end of the probe;
   a mixer which receives the reflected signal and a reference signal which is a portion of the output microwave radiation of the microwave radiation source, and which mixer reduces the frequency of the reflected signal and reference signal, the mixer having
 a first input selectively connected to receive the reflected signal or the reference signal,
 a second input connected to receive a mixing down signal, and
 an output for a mixed down reference signal and a mixed down reflected signal;
a reflected radiation detector connected to the output of the mixer to receive the mixed down reflected signal and the mixed down reference signal, where the detector detects the magnitude and phase of both the mixed down reflected signal and the mixed down reference signal; and
a tissue classifier which:
 classifies the region of tissue in direct contact with the distal end of the probe into a tissue type or tissue state based on a complex impedance of the region of tissue in direct contact with the distal end of the probe calculated from the magnitude and phase of the mixed down reflected and reference signals detected by the detector, and on a calibration value, obtained by measuring the impedance at the distal end of the probe for a known impedance, to which the calculated complex impedance is referenced, and
 displays the tissue type or tissue state of the region of tissue in direct contact with the distal end of the probe on a display.

2. A tissue classifying apparatus according to claim 1,
 further including a phase comparator and a local oscillator, the phase comparator being connected to receive a portion of the output microwave radiation from the microwave radiation source and a stable signal from the local oscillator and output a control signal based on a comparison of the output microwave radiation and stable signal, and
 wherein the microwave radiation source is phase locked to a single frequency based on the control signal output by the phase comparator.

3. A tissue classifying apparatus according to claim 1, wherein the tissue classifier compares the calculated complex impedance with a first set of data relating to known or theoretical values for the complex impedance of one or more tissues types.

4. A tissue classifying apparatus according to claim 1, wherein the tissue classifier classifies tissue by comparing the calculated complex impedance with values in a table assigning predetermined values or ranges of values to different tissue types.

5. A tissue classifying apparatus according to claim 1, further comprising an impedance adjuster having an adjustable complex impedance, said impedance adjuster being located between said source and said probe.

6. A tissue classifying apparatus according to claim 1, said cable having a phase stability of +/−5 degrees at the frequency of the microwave radiation output by the microwave radiation source.

7. A tissue classifying apparatus according to claim 6 wherein the cable is connected to an impedance adjuster having an adjustable complex impedance, said impedance adjuster being located between said source and said probe.

8. A tissue classifying apparatus according to claim 7, further including a power amplifier connected between the microwave radiation source and the probe, and wherein the power amplifier is selectively operable at a power level for ablating tissue.

9. A tissue classifying apparatus according to claim 8 wherein the power amplifier has two selectable power levels, whereby the apparatus has an ablation mode corresponding to a first selectable power level for ablating the tissue at the distal end of the probe and a tissue characterizing mode at the distal end of the probe, the amplitude of the microwave radiation delivered by the probe being higher in the ablation mode than in the tissue characterizing mode.

10. A tissue classifying apparatus according to claim 9, further comprising one of:
 (i) a variable amplifier for amplifying the reflected microwave radiation before it reaches the detector when the apparatus is in the tissue classification mode, and
 (ii) a variable attenuator for attenuating the reflected microwave radiation before it reaches the detector when the apparatus is in the tissue ablation mode.

11. A tissue classifying apparatus according to claim 8,
 further including an additional microwave radiation source for outputting ablation microwave radiation having a frequency different from the frequency of the output microwave radiation, and
 wherein the ablation microwave radiation is directed to the probe when in the probe is in an ablation mode.

12. A tissue classifying apparatus according to claim 11 said cable having a phase stability of +/−5 degrees at the frequency of the second source of microwave radiation.

13. A tissue classifying apparatus according to claim 1 comprising a voltage-controlled oscillator for outputting the mixing down signal, the voltage-controlled oscillator being connected in a phase locked loop that controls the frequency of the mixing down signal on the basis of the frequency of the microwave radiation output by the microwave radiation source.

14. A method of classifying tissue comprising the steps of:
 inserting a distal end of a probe into direct contact with a region of tissue to be classified, the distal end being fitted to the probe and being made from a rigid low loss dielectric ceramic,
 directing microwave radiation having a frequency in the range of 5 to 60 GHz from a microwave source, through a cable having a high phase stability under flexure connected to said probe, and into the region of tissue,
 receiving a reflected signal in a mixer, the reflected signal comprising microwave radiation reflected from the region of tissue in direct contact with the distal end of the probe back through the probe,
 receiving a reference signal in the mixer, the reference signal comprising a portion of the microwave radiation from the microwave source,
 outputting a mixing down signal from a voltage-controlled oscillator to the mixer,
 reducing with the mixer the frequency of the reflected signal and the reference signal by mixing the reflected signal and the reference signal with the mixing down signal,
 detecting the magnitude and phase of both the mixed down reflected signal and the mixed down reference signal in a reflected radiation detector,
 calculating a complex impedance of the region of tissue in direct contact with the distal end of the probe from the magnitude and phase of the mixed down reflected signal and the mixed down reference signal,
 classifying the tissue type or tissue state of the region of tissue in direct contact with the distal end of the probe based on the calculated complex impedance, and on a calibration value, obtained by measuring the impedance at the distal end of the probe for a known impedance, to which the calculated complex impedance is referenced, and displaying the tissue type or tissue state of the region of tissue in direct contact with the distal end of the probe on a display.

15. A method of ablating tissue carrying out the steps of claim 14 with microwave radiation of a first power in order to classify tissue and then ablating the tissue, by directing microwave radiation of a second power greater than said first power, down the same probe or another probe inserted into said tissue.

16. A method of ablating tissue according to claim 14 including the steps of:

connecting the voltage-controlled oscillator in a phase locked loop, and controlling the frequency of the mixing down signal on the basis of the frequency of the microwave radiation from the microwave source.

* * * * *